US011037673B2

(12) United States Patent
Cannady et al.

(10) Patent No.: US 11,037,673 B2
(45) Date of Patent: Jun. 15, 2021

(54) SYSTEMS AND METHODS FOR TRACKING SURGICAL INVENTORY AND STERILIZATION

(71) Applicant: Materials Management Microsystems, Inc., Mequon, WI (US)

(72) Inventors: Clay Cannady, Lake Forest, IL (US); Nathan Becker, Monrovia, CA (US)

(73) Assignee: Materials Management Microsystems, Inc., Mequon, WI (US)

( * ) Notice: Subject to any disclaimer, the term of this patent is extended or adjusted under 35 U.S.C. 154(b) by 1040 days.

(21) Appl. No.: 15/257,048

(22) Filed: Sep. 6, 2016

(65) Prior Publication Data
US 2017/0068788 A1 Mar. 9, 2017

Related U.S. Application Data

(60) Provisional application No. 62/214,644, filed on Sep. 4, 2015.

(51) Int. Cl.
| | | |
|---|---|---|
| *G16H 40/20* | (2018.01) | |
| *G06Q 10/08* | (2012.01) | |
| *A61B 90/96* | (2016.01) | |
| *A61L 2/24* | (2006.01) | |
| *G06F 19/00* | (2018.01) | |

(52) U.S. Cl.
CPC .............. *G16H 40/20* (2018.01); *A61B 90/96* (2016.02); *A61L 2/24* (2013.01); *G06F 19/00* (2013.01); *G06Q 10/08* (2013.01); *A61F 2250/0086* (2013.01); *A61L 2202/14* (2013.01); *A61L 2202/24* (2013.01)

(58) Field of Classification Search
CPC ........ G06Q 10/06; G16H 40/20; A61B 90/96; G06F 19/325
See application file for complete search history.

(56) References Cited

U.S. PATENT DOCUMENTS

| | | | |
|---|---|---|---|
| 4,937,743 A | 6/1990 | Rassman et al. | |
| 5,374,813 A * | 12/1994 | Shipp ..................... | G06Q 10/08 235/375 |
| 5,842,173 A | 11/1998 | Strum et al. | |
| 6,389,454 B1 | 5/2002 | Ralston et al. | |

(Continued)

OTHER PUBLICATIONS

Materials Management Microsystems, FAQ (Mar. 2010), retrieved from URL <http://www.microsystems.com/faq/> on Jul. 24, 2019 (hereinafter referred to as MMM).*

(Continued)

*Primary Examiner* — Julie M Shanker
(74) *Attorney, Agent, or Firm* — Andrus Intellectual Property Law

(57) ABSTRACT

A sterile processing information system receives data from a hospital clinical system representing scheduled surgical procedures and identified hospital owned assets for the respective surgical procedures, and also receives third party asset data electronically in a parsable data format from the vendor inventory management system representing scheduled surgical procedures and the third party assets for the respective surgical procedure. The system manages the sterile processing of both hospital and third party assets, and in particular creates a count sheet with a barcode for each of the third party assets.

10 Claims, 24 Drawing Sheets

(56) References Cited

U.S. PATENT DOCUMENTS

| | | | |
|---|---|---|---|
| 6,485,979 B1 * | 11/2002 | Kippenhan | A61L 2/24 422/403 |
| 6,801,913 B2 * | 10/2004 | Matsumura | G06F 19/3418 |
| 7,518,502 B2 | 4/2009 | Austin et al. | |
| 8,249,895 B2 | 8/2012 | Faulkner et al. | |
| 8,423,377 B2 | 4/2013 | Roady | |
| 8,429,033 B2 | 4/2013 | Kreifels et al. | |
| 8,595,029 B2 | 11/2013 | Pederson et al. | |
| 8,671,009 B1 | 3/2014 | Coley et al. | |
| 8,805,900 B2 | 8/2014 | Curran et al. | |
| 2002/0055918 A1 | 5/2002 | Hlathein et al. | |
| 2003/0083902 A1 * | 5/2003 | Hehenberger | G06Q 10/087 705/2 |
| 2003/0182299 A1 * | 9/2003 | Burns | G06Q 10/08 |
| 2003/0187586 A1 * | 10/2003 | Katzenmaier | A61L 2/24 702/19 |
| 2005/0149379 A1 | 7/2005 | Cyr et al. | |
| 2007/0237674 A1 * | 10/2007 | Jung | A61L 2/0011 422/62 |
| 2008/0030345 A1 * | 2/2008 | Austin | A61B 90/90 340/572.8 |
| 2009/0089092 A1 * | 4/2009 | Johnson | G06Q 10/06 705/2 |
| 2010/0161345 A1 * | 6/2010 | Cain | G06F 19/328 705/2 |
| 2010/0274591 A1 * | 10/2010 | Wells | G06Q 10/06 705/3 |
| 2011/0208535 A1 | 8/2011 | Le Couedic et al. | |
| 2012/0101842 A1 * | 4/2012 | Montano | G06Q 10/06 705/2 |
| 2012/0109679 A1 | 5/2012 | Massoumi et al. | |
| 2012/0316987 A1 * | 12/2012 | DeBusk | G06Q 10/08 705/26.8 |
| 2013/0066647 A1 | 3/2013 | Andrie et al. | |
| 2013/0253941 A1 * | 9/2013 | Stickler | G06Q 10/06311 705/2 |
| 2014/0125482 A1 * | 5/2014 | Rigsby | A61B 17/7001 340/539.13 |
| 2014/0188496 A1 | 7/2014 | Ramsey et al. | |
| 2017/0061375 A1 * | 3/2017 | Laster | G16H 50/30 |

OTHER PUBLICATIONS

Rose Seavey, RN, MBA, CNOR, CRCST, CSPDT, "Getting a Handle on Loaner Instrumentation," Mar. 2011 (hereinafter referred to as Seavey).*

Seavey, Getting a Handle on Loaner Instrumentation, healthVIE.com, pp. 70-90, Mar. 2011.

Excerpts from SPM software in the form of screen shots, in public use in 2015 (admitted prior art).

Step-by-step instructions published by Materials Management Microsystems, Inc., Attaching Pictures or Files to Loaners (admitted prior art).

Step-by-step instructions published by Materials Management Microsystems, Inc., Entering a New Loaner Product (admitted prior art).

Step-by-step instructions published by Materials Management Microsystems, Inc., Marking Loaners as Ready for Pickup (admitted prior art).

Step-by-step instructions published by Materials Management Microsystems, Inc., Marking Loaners as Returned (admitted prior art).

Step-by-step instructions published by Materials Management Microsystems, Inc., Placing a New Loaner Order (admitted prior art).

Step-by-step instructions published by Materials Management Microsystems, Inc., Printing Loaner Labels (admitted prior art).

Step-by-step instructions published by Materials Management Microsystems, Inc., Receiving a Loaner Order that was Placed in SPM (admitted prior art).

Step-by-step instructions published by Materials Management Microsystems, Inc., Receiving a New Loaner Order (admitted prior art).

* cited by examiner

CANNULATED SCREW SYSTEM 3.5MM/4.0MM

CASE 1147-35-01 Screw Caddy

| CAN2 | 1 SET | CANNULATED SCREW SYSTEM 3.5MM/4.0MM INSTRUMENTS BASE TRAY & CREW CADDY 1147-xx-35 & 1147-XX36 | | CANNULATED SCREW SYSTEM 3.5MM/4.0MM CREW CADDY 1147-xx-35 & | |
|---|---|---|---|---|---|
| 1 | 00-1147-010-35 | 3.5 CANN DIAMETER GAUGE 10 3 EA | | 23 | 00-1147-012-36 | 3.6 CANN FULL THREAD 12 2 EA |
| 2 | 00-1147-012-35 | 3.5 CANN DIAMETER GAUGE 12 3 EA | | 24 | 00-1147-014-36 | 3.6 CANN FULL THREAD 14 2 EA |
| 3 | 00-1147-014-35 | 3.5 CANN DIAMETER GAUGE 14 3 EA | | 25 | 00-1147-016-36 | 3.6 CANN FULL THREAD 16 2 EA |
| 4 | 00-1147-016-35 | 3.5 CANN DIAMETER GAUGE 16 3 EA | | 26 | 00-1147-018-36 | 3.6 CANN FULL THREAD 18 2 EA |
| 5 | 00-1147-018-35 | 3.5 CANN DIAMETER GAUGE 18 3 EA | | 27 | 00-1147-020-36 | 3.6 CANN FULL THREAD 20 2 EA |
| 6 | 00-1147-020-35 | 3.5 CANN DIAMETER GAUGE 20 3 EA | | 28 | 00-1147-022-36 | 3.6 CANN FULL THREAD 22 2 EA |
| 7 | 00-1147-022-35 | 3.5 CANN DIAMETER GAUGE 22 3 EA | | 29 | 00-1147-024-36 | 3.6 CANN FULL THREAD 24 2 EA |
| 8 | 00-1147-024-35 | 3.5 CANN DIAMETER GAUGE 24 3 EA | | 30 | 00-1147-026-36 | 3.6 CANN FULL THREAD 26 2 EA |
| 9 | 00-1147-026-35 | 3.5 CANN DIAMETER GAUGE 26 3 EA | | 31 | 00-1147-028-36 | 3.6 CANN FULL THREAD 28 2 EA |
| 10 | 00-1147-028-35 | 3.5 CANN DIAMETER GAUGE 28 3 EA | | 32 | 00-1147-030-36 | 3.6 CANN FULL THREAD 30 2 EA |
| 11 | 00-1147-030-35 | 3.5 CANN DIAMETER GAUGE 30 3 EA | | 33 | 00-1147-032-36 | 3.6 CANN FULL THREAD 32 2 EA |
| 12 | 00-1147-032-35 | 3.5 CANN DIAMETER GAUGE 32 3 EA | | 34 | 00-1147-034-36 | 3.6 CANN FULL THREAD 34 2 EA |
| 13 | 00-1147-034-35 | 3.5 CANN DIAMETER GAUGE 34 3 EA | | 35 | 00-1147-036-36 | 3.6 CANN FULL THREAD 36 2 EA |
| 14 | 00-1147-036-35 | 3.5 CANN DIAMETER GAUGE 36 3 EA | | 36 | 00-1147-0138-36 | 3.6 CANN FULL THREAD 38 2 EA |
| 15 | 00-1147-038-35 | 3.5 CANN DIAMETER GAUGE 38 3 EA | | 37 | 00-1147-040-36 | 3.6 CANN FULL THREAD 40 2 EA |
| 16 | 00-1147-040-35 | 3.5 CANN DIAMETER GAUGE 40 3 EA | | 38 | 00-1147-0142-36 | 3.6 CANN FULL THREAD 42 2 EA |
| 17 | 00-1147-042-35 | 3.5 CANN DIAMETER GAUGE 42 3 EA | | 39 | 00-1147-044-36 | 3.6 CANN FULL THREAD 44 2 EA |
| 18 | 00-1147-044-35 | 3.5 CANN DIAMETER GAUGE 44 3 EA | | 40 | 00-1147-046-36 | 3.6 CANN FULL THREAD 46 2 EA |
| 19 | 00-1147-046-35 | 3.5 CANN DIAMETER GAUGE 46 3 EA | | 41 | 00-1147-048-36 | 3.6 CANN FULL THREAD 48 2 EA |
| 20 | 00-1147-048-35 | 3.5 CANN DIAMETER GAUGE 48 3 EA | | 42 | 00-1147-050-36 | 3.6 CANN FULL THREAD 50 2 EA |
| 21 | 00-1147-050-35 | 3.5 CANN DIAMETER GAUGE 50 3 EA | | 43 | NA | LID FOR SCREW CADDY |
| 22 | 00-1147-010-36 | 3.6 CANN FULL THREAD 10 2 EA | | | | |

Fig. 7

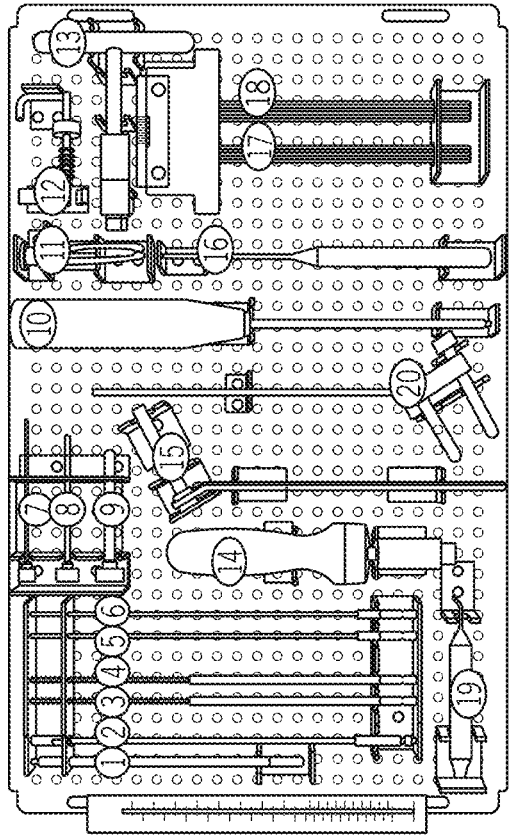

| CAN2 | 1 SET | INSTRUMENTS TOP TRAY | | | |
|---|---|---|---|---|---|
| 1 | 00-1147-046-00 | CANN DRIVER Q-2 2.5MM HEX | 11 | 00-1147-081-00 | SCREW HOLDING SLEEVE |
| 2 | 00-1147-033-00 | CANN COUNTERSINK Q-C | 12 | 00-1147-096-00 | WASHER 6 EA |
| 3 | 00-1147-038-00 | CANN TAP 1-C 4.0MM | 13 | 00-1147-050-00 | CANN T-HANDLE Q-C |
| 4 | 00-1147-037-00 | CANN TAP Q-C 3.5MM | 14 | 00-1147-053-00 | CANN RATCHET HANDLE Q-C |
| 5 | 00-1147-026-00 | 2.7 CANN DRILL FOR 3.5MM /4.0MM CANN SC | 15 | 00-1147-002-00 | PERCT CANNULA FOR 3.5/4.0 SCREWS |
| 6 | 00-1147-026-00 | 2.7 CANN DRILL FOR 3.5MM /4.0MM CANN SC | 16 | 00-1147-019-00 | DEPTH GAUGE |
| 7 | 00-1147-066-00 | TROCAR | 17 | 00-1147-084-00 | GUIDE PIN 1.6MMX6IN PARTIAL THREAD 10 |
| 8 | 00-1147-006-00 | GUIDE PIN SLEEVE | 18 | 00-1147-094-00 | GUIDE PIN 1.6MMX6IN SMOOTH 10 EA |
| 9 | 00-1147-011-00 | DRILL SLEEVE | 19 | 00-1147-080-00 | SCREW FORCEPS |
| 10 | 00-1147-062-00 | CANN SCREWDRIVER 2.5MM HEX | 20 | 00-1147-057-00 | ADJUSTABLE PARALLEL PIN GUIDE |

Fig. 11A

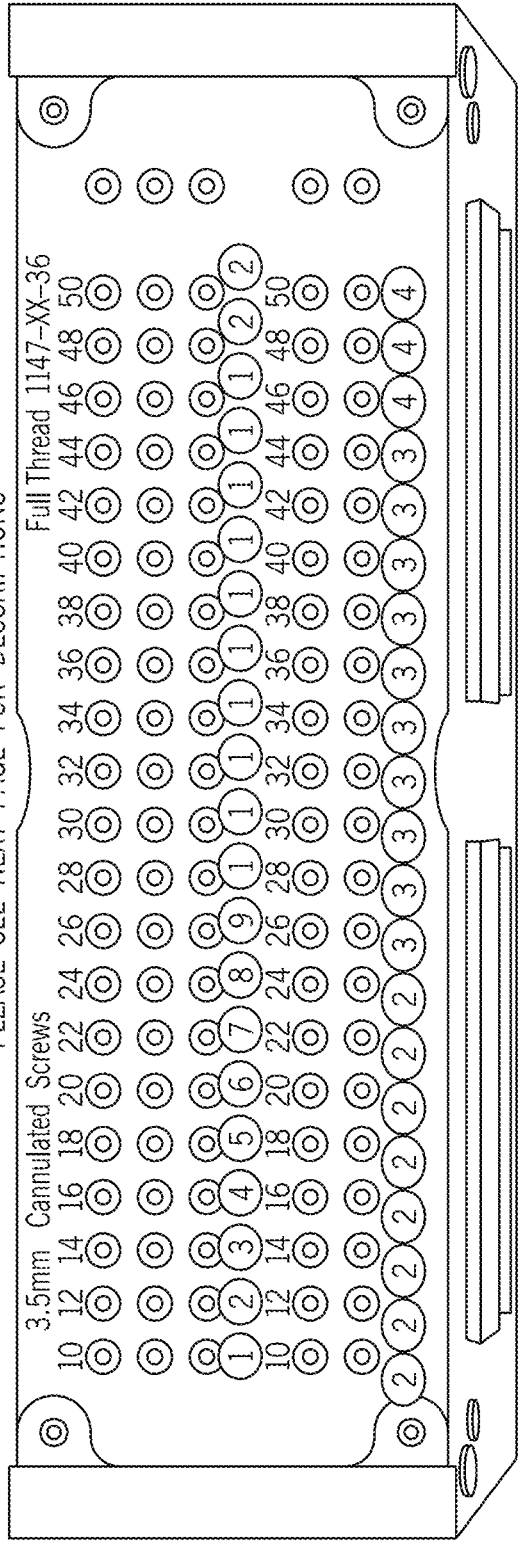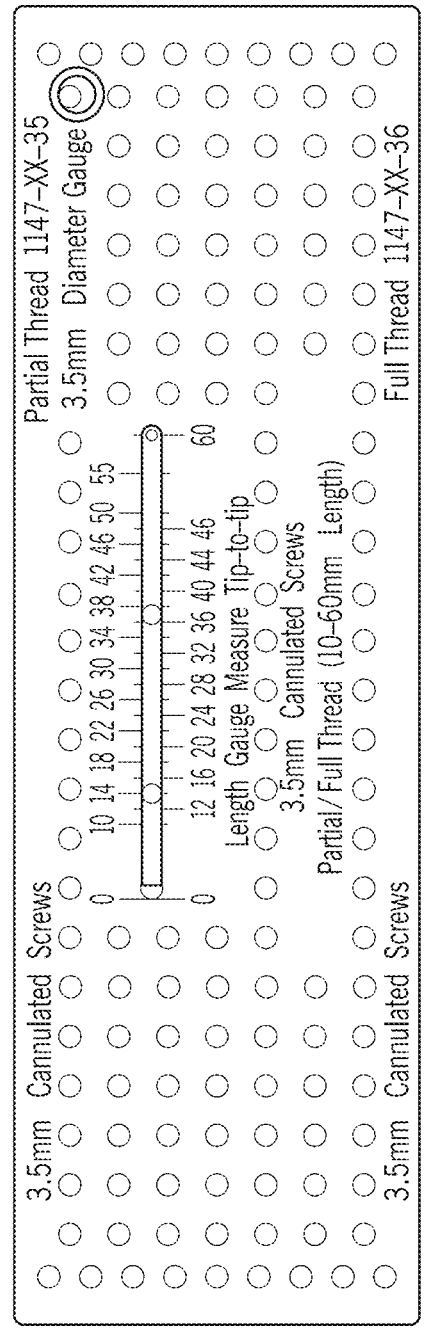
Fig. 11B

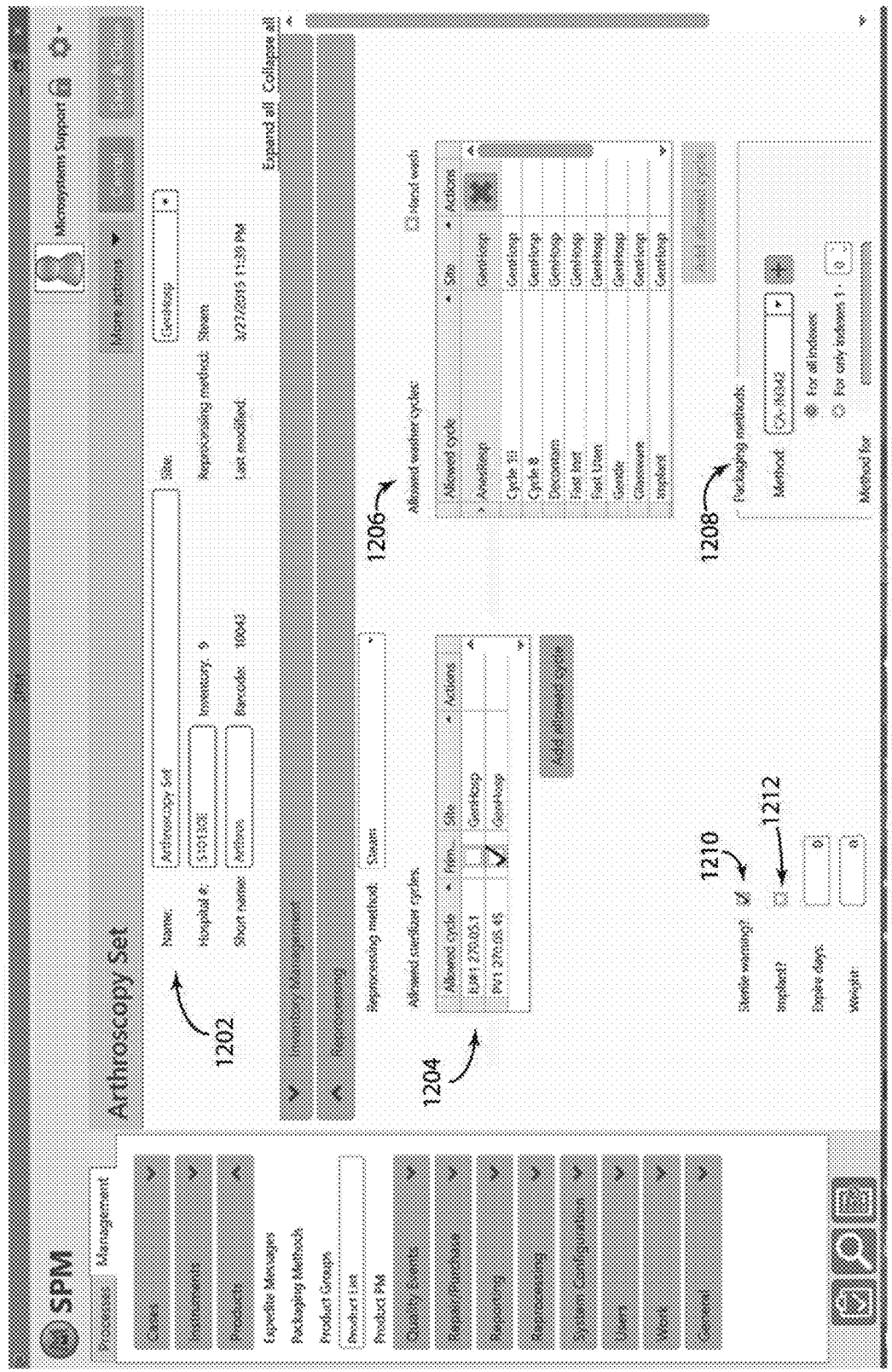
Fig. 12A -- PRIOR ART --

Fig. 12B -- PRIOR ART --

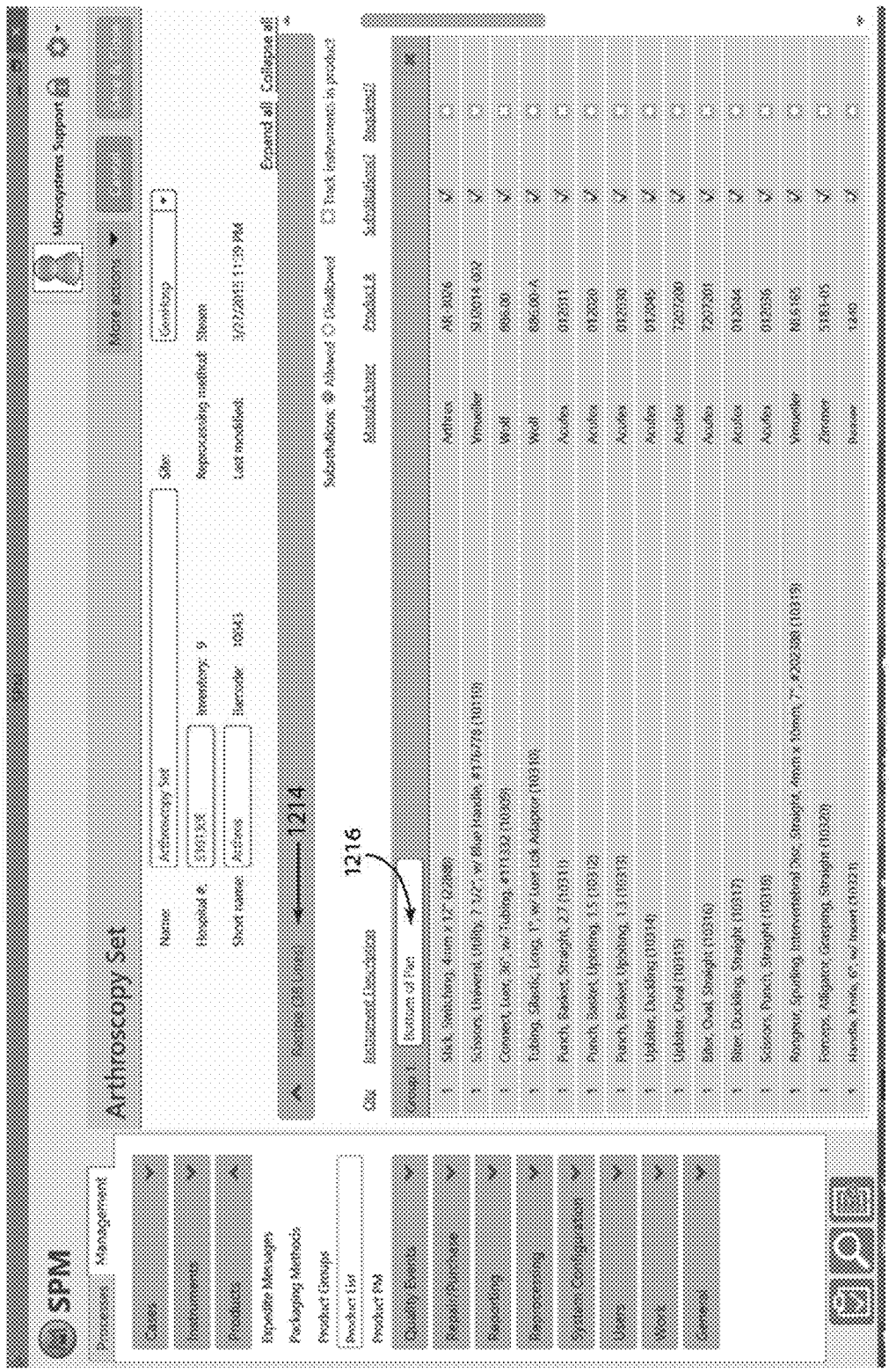
Fig. 12C -- PRIOR ART --

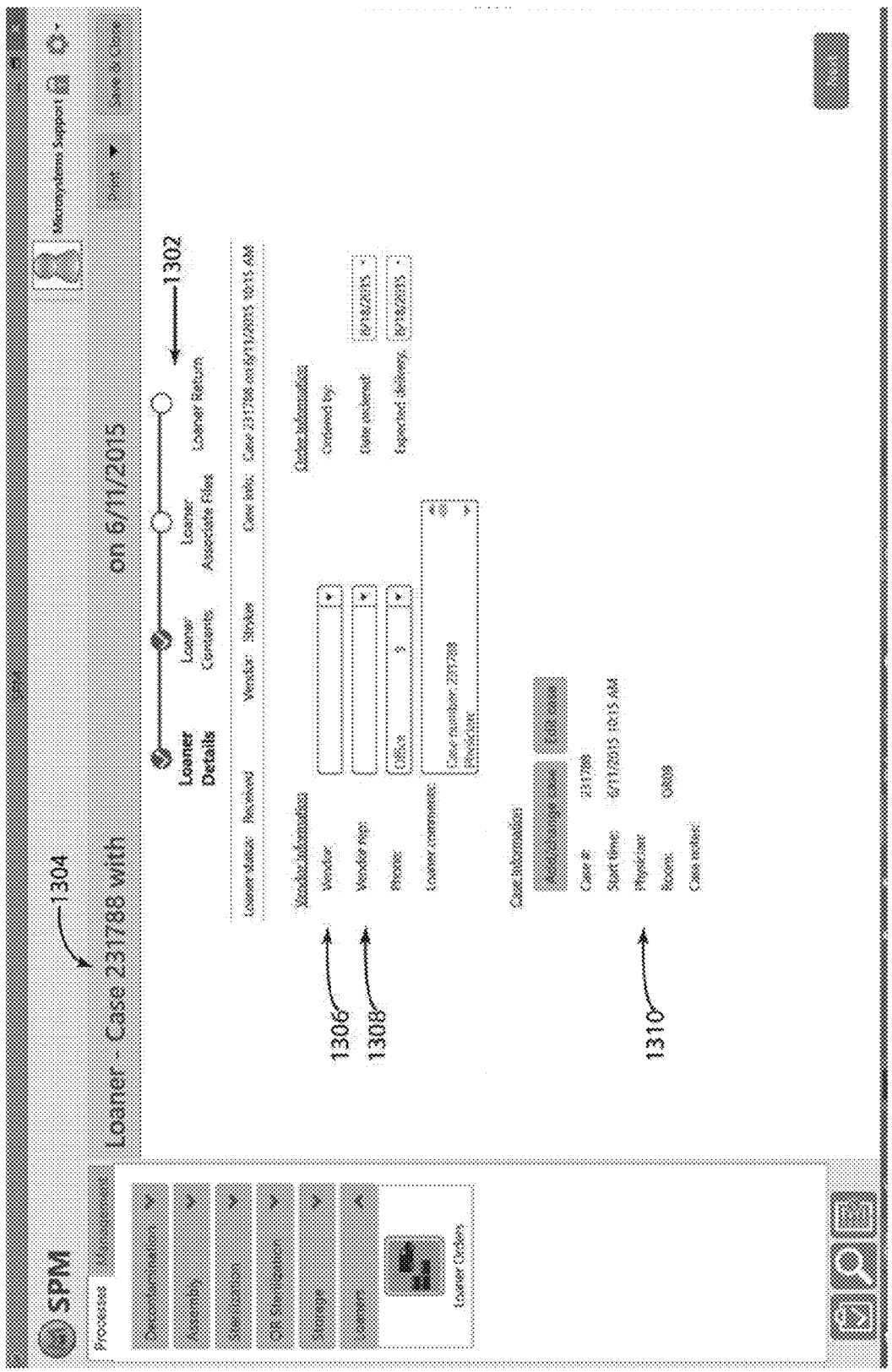
Fig. 13A -- PRIOR ART --

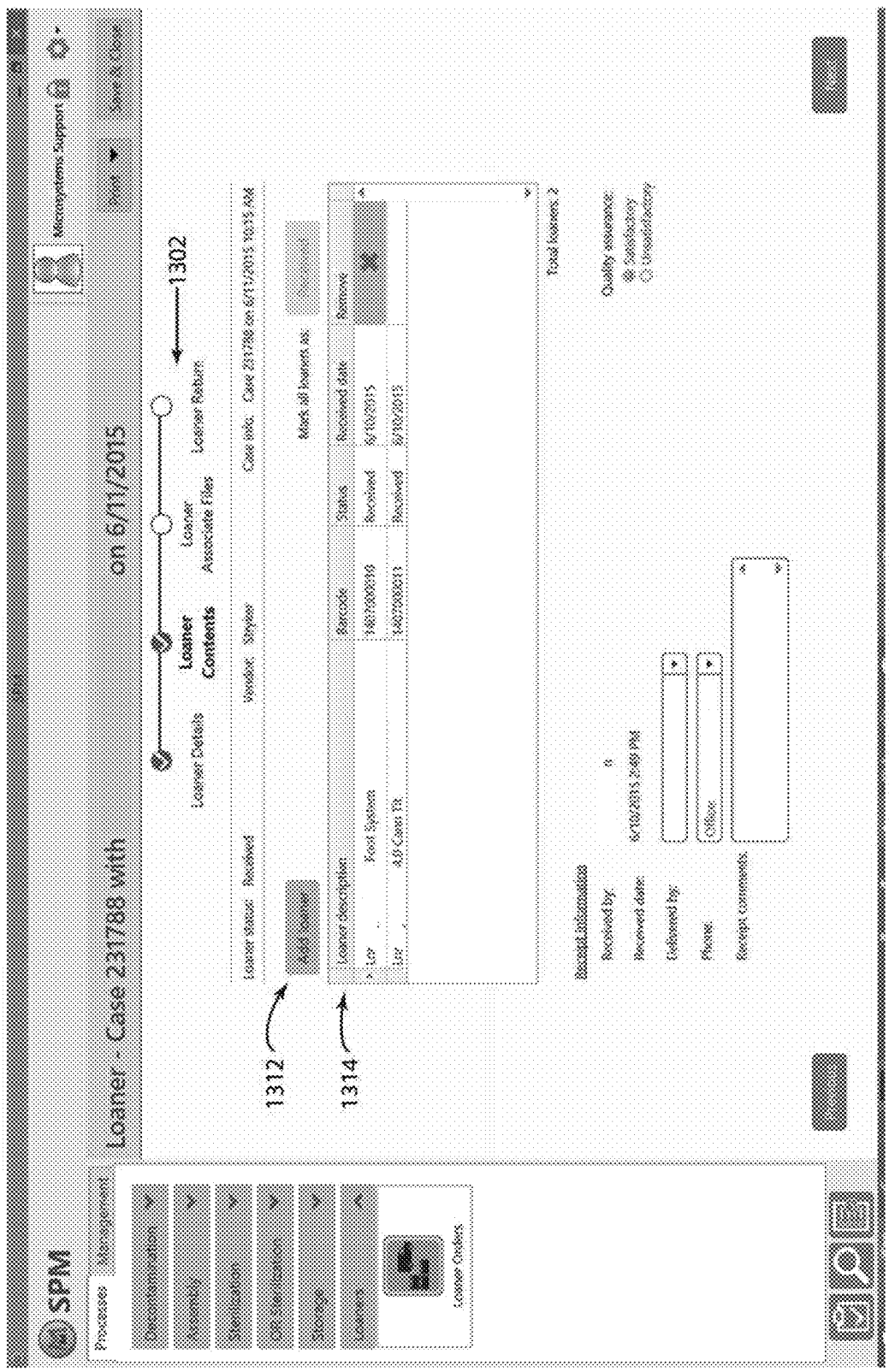
Fig. 13B -- PRIOR ART --

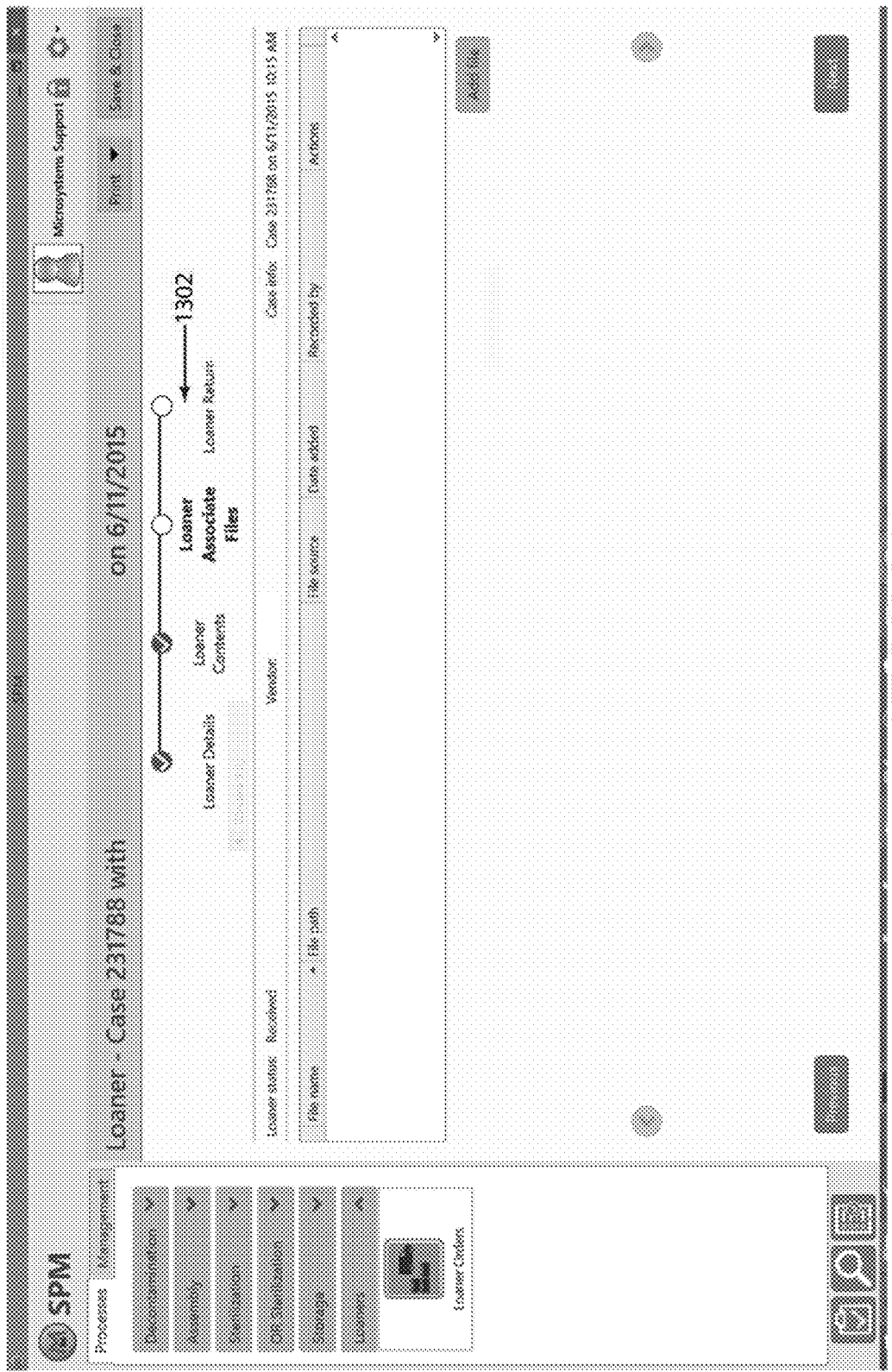
Fig. 13C -- PRIOR ART --

SYSTEMS AND METHODS FOR TRACKING SURGICAL INVENTORY AND STERILIZATION

FIELD OF THE DISCLOSURE

The present disclosure relates to tracking surgical inventory and sterilization. More particularly, it relates to systems and methods for tracking instruments, implants and consumables used by the hospital, including assets owned by the hospital as well as instrumentation loaner sets, implants and other consumables owned by third party vendors.

BACKGROUND

Hospitals with surgical facilities own a large inventory of surgical tools and consumables used in surgical procedures. These are documented and managed as part of a hospital inventory. When a surgery is scheduled, a hospital clinical system uses a "Preference Card" system to document the room(s), personnel, instruments, and consumables of the hospital required to perform the scheduled surgery. The "Preference Card" system, however, is typically limited only to those instruments and/or consumables owned by the hospital, and therefore in the hospital's inventory.

Currently available sterile processing information systems facilitate the work of the sterile processing department (SPD) by managing the status and location of instruments and instrument sets within the SPD at any given time. For owned assets, the sterile processing information system further provides the instructions for use (IFU) associated with each owned asset and help SPD personnel to optimize a task of the SPD for preparation, packaging, sterilization, and delivery.

FIGS. 8A and 8B depict an exemplary embodiment of an SPD 800. The SPD 800 exemplarily include storage 802 for hospital owned assets and location for SPD staff to perform the operations required of the SPD. These include cleaning 804, packaging 806, and sterilization 808. The sterilization at 808 may be performed by a variety of available sterilizers, including, but not limited to steam sterilizer, plasma sterilizers, and chemical sterilization treatments. Additionally, the SPD 800 may include a drop off vestibule 810 wherein loaner sets of instrumentation may be received or delivered to third party. The SPD 800 further includes decontamination areas for initial cleaning of instruments at 812. In the SPD, computers 814 exemplarily embodying the sterile processing information system are distributed at a plurality of locations, including many of the work stations identified above. Additionally, barcode scanners 816 or other scanning input devices are located with the computers 814. As described in other embodiments herein, some locations may also include a printer 818. Thus, the sterile processing information system as described in further detail herein operates exemplarily on a distributed network exemplarily throughout the SPD, although in other embodiments, the sterile processing information system may operate across a network with computer locations in other parts of the hospital as well.

Figure 12B:
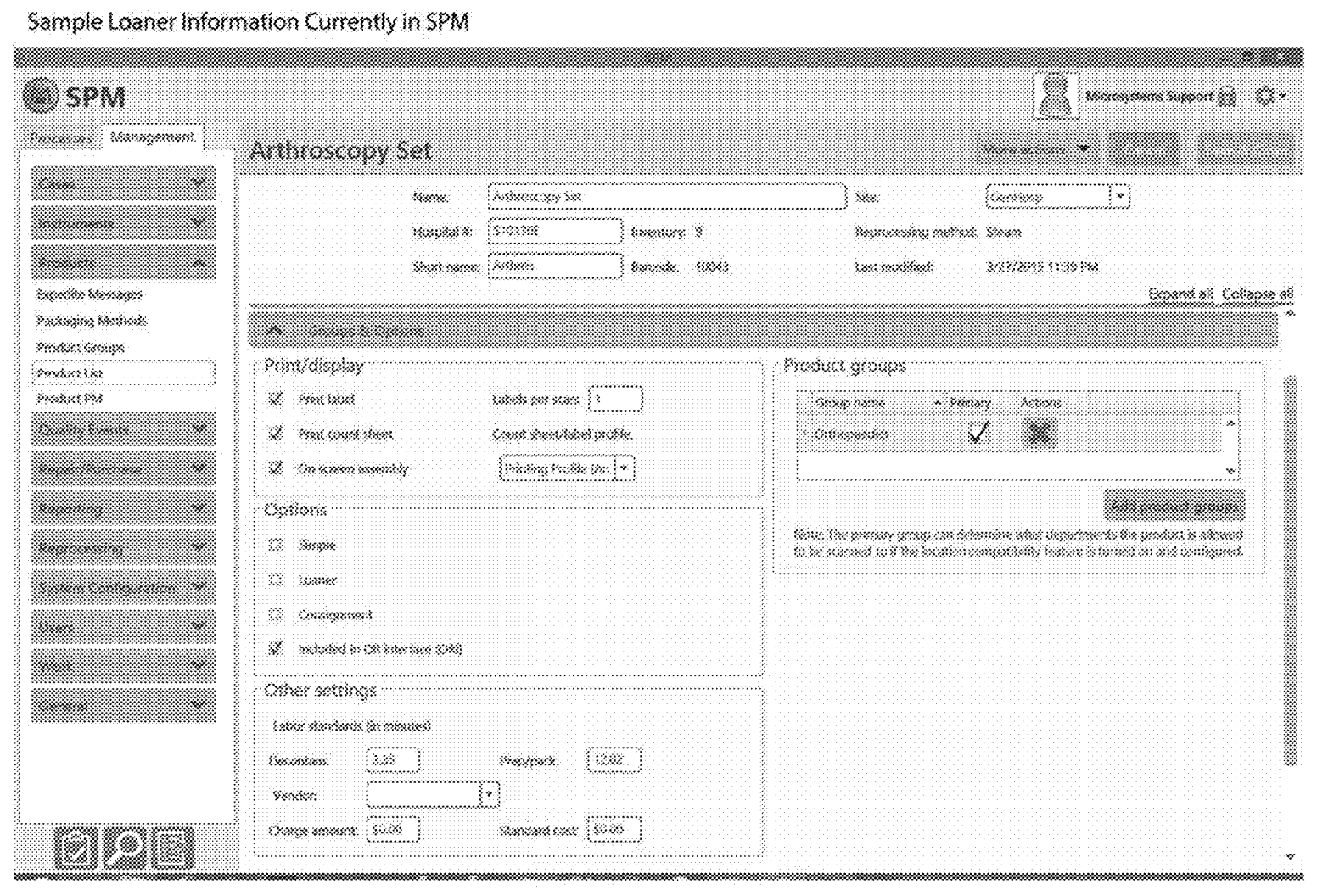
Figure 12D:
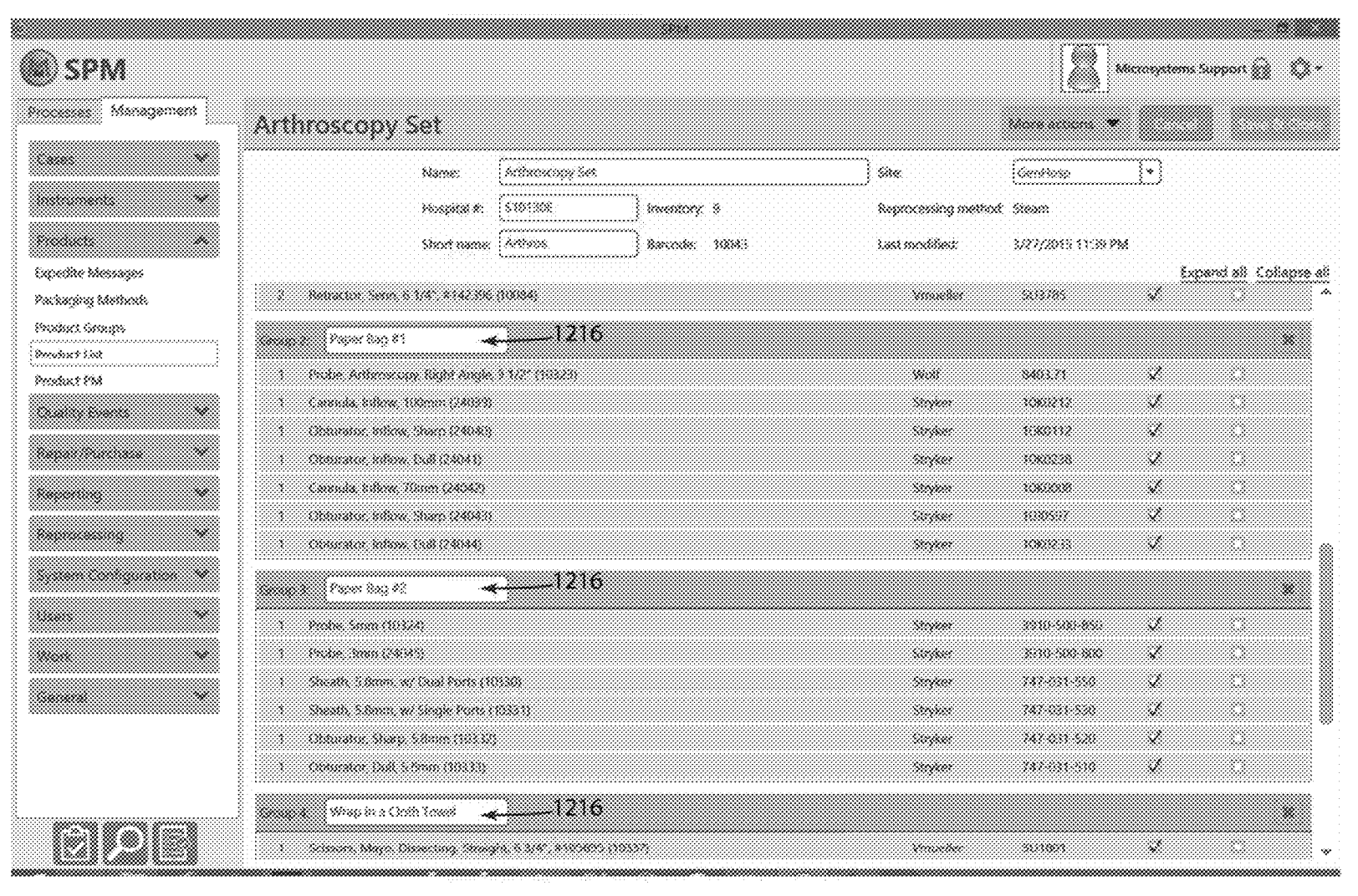
Figure 12E:
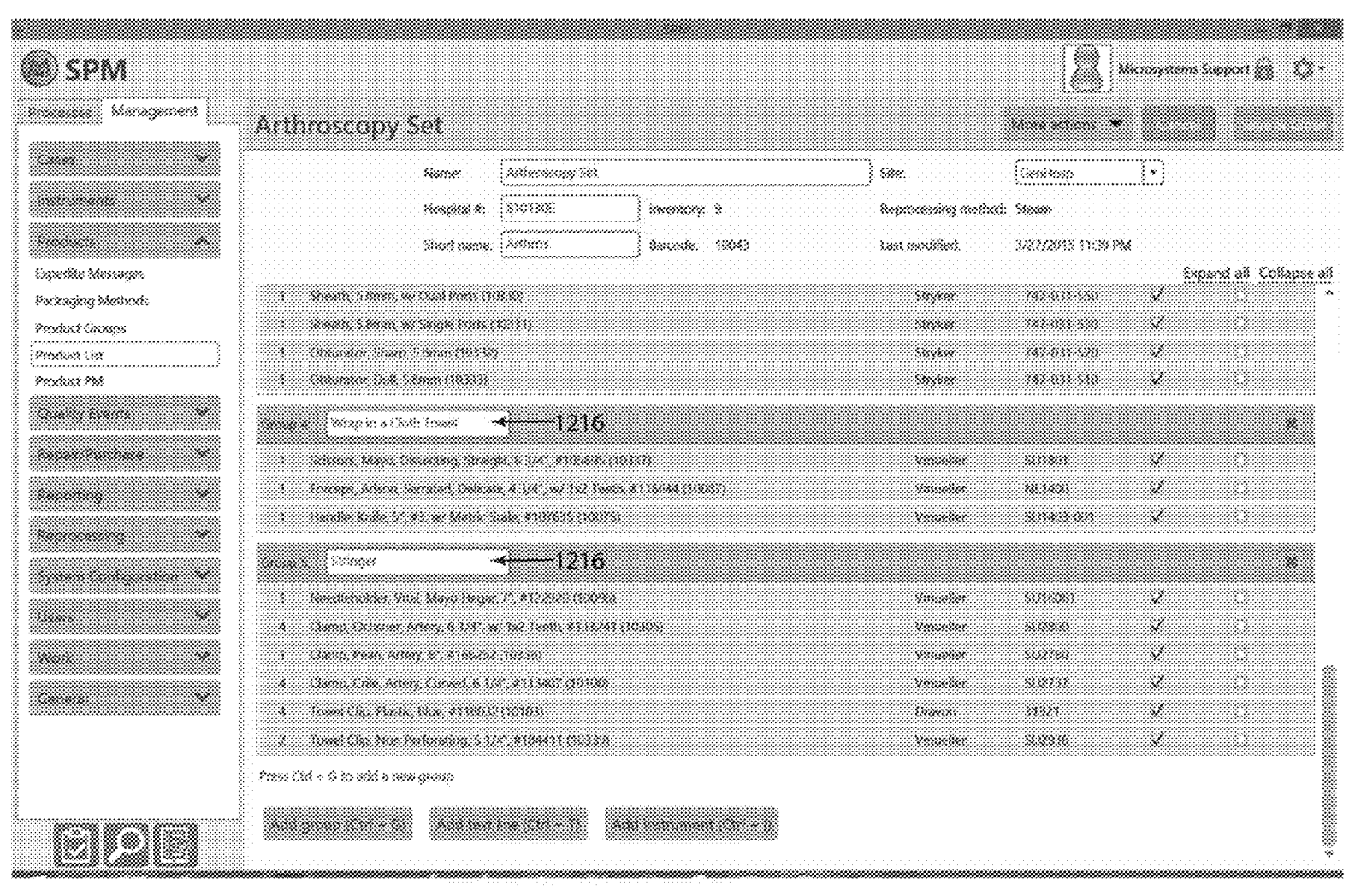

FIGS. 12A-12D depict exemplary screen shots of a sterile processing information system when used to handle the sterile processing of a hospital owned asset, e.g. an arthroscopy set. When a hospital owned asset such as the arthroscopy set is processed by the SPD using the sterile processing information system all of the information required for sterile processing of the hospital owned instruments are already known and populated into the displays as presented in FIGS. 12A-12D. For example, the set identification information 1202, the allowed sterilizer cycle 1204, allowed washer cycles 1206, and packaging methods 1208 are provided to the SPD staff through the sterile processing information system. The sterile processing information system further provides indications of whether they must be sterilized at 1210 and if the instrument set includes an implant at 1212. Importantly, the sterile processing information system provides a recipe for the instrument set at 1214. This recipe at 1214 identifies each of the instruments that must be included in the instrument set, the group within which the instrument is located along with a location 1216 of that group within the instrument set. Hospital owned assets are therefore quickly and efficiently processed by SPD personnel by accessing the necessary information from the sterile processing information system relevant to each work station within the SPD and hospital owned assets are processed.

Typically, a barcode is assigned to each instrument set or individual peel package item. The barcodes may be scanned at each step of the sterilization process to note the location of the instrument and sterilization and/or packaging status of the instrument. Before the sterile processing information system permits a sterilization load to be closed for sterilization, the sterile processing information system verifies all identified instrument sets and peel packages for special sterilization requirements according to the IFU and alerts the SPD personnel to these requirements before a sterilizer cycle is run. The sterile processing information system further maintains a record of the sterilization treatment received by each of the instruments or instrument sets.

At least three trends in healthcare services create problems for hospitals using the "Preference Card" system as it is currently available. First, many surgeries require highly specialized instrumentation specific to a single procedure or the use of a particular consumable such as an implant (e.g. replacement hip). Such specialized equipment are typically provided by the vendor of the implant as a vendor "loaner set" conditional with the purchase of the implant used in the surgery. Second, a hospital may own a limited number of instrument sets of particular instruments while a surgical schedule may require additional instrument sets for a particularly busy surgical schedule. In such events, the hospital may borrow instrument sets from another facility rather than make an additional capital purchase of instruments. Finally, surgical consumables, for example, surgical screws or pins may be provided by a vendor on consignment so that a wide variety of e.g. screw sizes, shapes, or properties are available during a surgery and the hospital pays for the consumables used when they are replaced by the vendor.

While each of these activities present challenges in instrumentation management and documentation, loaner sets of instrumentation present particular challenges stemming from the fact that they are not owned assets of the hospital which is ultimately responsible for sterilization and tracking of the instruments and documentation thereof. Surgical technology is rapidly changing and improving and modern surgery often requires very intricate and procedure specific instrumentation. As noted above, particularly in the event of implant surgery, the use of any one specific implant is performed so infrequently that a hospital cannot afford to purchase or store all of the necessary instruments specific to that procedure or implant. Thus, the implant vendor typically provides the specialized instrumentation as a loaner set of instrumentation. Guidelines recommend that each healthcare facility have a well-defined instrument management program and multi-disciplinary policy on the management of loaner instrumentation, implants, and equipment, and the borrower is ultimately responsible to ensure that the loaner sets are safe and free of contamination when used on their patients. This responsibility requires that the borrower facility ensure that the items are safe for use on their patients by making sure the sterilization process is properly implemented and documented and that all of the borrowed items are traceable to the patient.

These tasks are challenging enough on their own, but create significant challenges when loaner sets of instrumentation and implants do not arrive in ample time to permit routine cleaning and terminal sterilization in house or the instrumentation of the loaner set is unfamiliar to the sterilization staff, requiring the verification of the required sterilization processes and times to ensure that the items are free of contamination.

In doing so, the hospital facility must process and handle loaner set instrumentation to ensure safe patient care. To ensure sterility of instruments and trays, the loaner set instrumentation must be cleaned, inspected, inventoried, wrapped, sterilized, cooled, implants quarantined until biological indicators (BI) are negative, documented, and tracked to the patient. However, the exact contents of loaner instrumentation are not known by the hospital until it is received prior to the surgery. Often, the loaner instrumentation does not arrive at the hospital until shortly before the scheduled surgery leaving insufficient time for integration into the processing of the hospital owned assets for the same surgery. Furthermore, as the contents of the loaner set is not known in advance, the processing of the loaner set must be entirely handled as a rush job, and SPD staff and resources must be put on hold to process the incoming loaner instrumentation. These rushed processes are less efficient as sterilization batches and processes are operated for speed and processing of the particular loaner set, rather than operated to maximize overall efficiency and cost effectiveness. Additionally, the manufacturer's written IFU for cleaning, packaging, and sterilizing must be followed and product sterilization testing must be performed to ensure that the loaner set instrumentation has been sterilized and verified in the required manners. Due to the specialization of the instruments in loaner sets, these sets often have sterilization requirements different than standard requirements used for more common instrumentation such as would be found in the hospital owned assets.

FIG. 13A depicts screen shots depicting an exemplary embodiment of how loaner sets are currently handled within an exemplary sterile processing information system. As can be seen from the screen shots at 13A-13C far less information is available for processing of the loaner set. Rather, at the top of the display, a generalized stage in the process of handling the loaner set is indicated at 1302 and the information provided is more generally directed to identification of the loaner set itself with a relevant case number at 1304, an identification of the vendor at 1306, a vendor representative at 1308, and an identification of the physician at 1310. As previously mentioned, when a loaner set is received by the SPD, exemplarily at the drop off location (810 in FIG. 8B), the contents of the loaner set must be manually entered into the system to provide any information regarding the loaner set to SPD personnel using the sterile processing information system. Loaner sets may exemplarily be added with the "add loaner" interface button at 1312 or selected from a list of available loaner descriptions at 1314, which may represent other loaner sets delivered for the same surgical case. FIGS. 14A and 14B exemplarily depict screen shots of a product identification as may be provided upon selection of one of the loaner sets available in the loaner set list 1314. In an exemplary embodiment, all of the information provided on these exemplary screen shots is manually entered upon intake and processing of the loaner set at the SPD. Exemplarily, the information entered by the SPD staff may come from a review of IFU materials physically provided along with the loaner sets. As can be seen through a comparison of the screen shots of 14A and 14B with the screen shots of 12A-12E rely upon SPD personnel correctly entering sufficient processing information and requirements to appropriately process the loaner set as a rush order. The recipe for the instrument set is notably absent in the screen shots of 14A and 14B as the exact contents of the loaner set is not known by the SPD, and it would represent too time consuming of an effort to identify, document, and enter each item received in the loaner set into the sterile processing information system. Rather, the loaner sets are handled on a set by set basis and the SPD personnel handling intake of the delivered loaner sets may generally document the contents of the received loaner set for example by taking a digital photograph of the open loaner set so that if the received contents must be verified, the digital photographs may be referenced at that time for retrospective identification. Referring to FIG. 13C, it is also to be noted that while a field exists, there is generally no associated files with the loaner set within the sterile processing information system although, in embodiments, this is where documented pictures of the contents of the loaner set may appear. However, no referential pictures, instructions for use or other documentation regarding the loaner set is available within the sterile processing information system.

As mentioned above, hospitals currently must rely on a patchwork application of the "Preference Card" system which only includes the instrumentation for a surgery that is available from the hospital's owned inventory, as well as the consumables managed internally by the hospital supply chain functions. The "Preference Card" system may indicate that other borrowed instrumentation or consigned or specialized consumables, including implants, may be used in the surgery but without further indication as to the instruments or consumables.

However, new processes are needed to incorporate unowned assets into the hospital sterile processing system. Embodiments as disclosed herein provide solutions to these problems as well as other solutions that improve management of instrument and consumable inventory, whether owned or unowned by the hospital.

SUMMARY OF THE INVENTION

In one aspect, the invention sterile processing information system that is capable of receiving data from a hospital clinical system and receiving and integrating third party asset data from a vendor inventory management system in a manner that enables more effective scheduling of sterile processing procedures in the hospital. Typically, a hospital clinical system is configured to receive clinician inputs to schedule surgical procedures and identify hospital owned assets required for the respective surgical procedures. In some instances, third parties use a vendor inventory management system configured to receive clinician inputs to schedule surgical procedures and identify third party assets required for the respective surgical procedures. These third party assets can constitute loaners instrument sets, implants or consumables provided by third parties for the respective surgical procedure. The invention is directed to scheduling sterilization of hospital owned and third party assets for surgery when the third party uses a vendor inventory management system.

The sterile processing information system receives data from the hospital clinical system representing scheduled surgical procedures and the identified hospital owned assets for the respective surgical procedures, as is known in the art. The sterile processing information system also receives third party asset data from the vendor inventory management system representing scheduled surgical procedures and the third party assets for the respective surgical procedures. This third party asset data is transmitted electronically in a parsable or structured data format, desirably in real time or on a periodic basis so that the sterile processing information system can receive the information as soon as reasonably possible, without having to wait for the delay and possible mistakes associated with human entry of data. The sterile processing information system contains a sterile processing database which is populated automatically with the data received from the hospital clinical system and also automatically with third party asset data received from the vendor inventory management system. The sterile processing information system is then able to generate a sterilization schedule for the hospital owned assets and the third party assets for the respective surgical procedures.

In one embodiment, the sterile processing information system includes an interface service configured to request for third party asset data from the vendor inventory management system periodically. The vendor inventory management system includes a web service application program interface (API) that transmits parsable third party asset data in structured format to the interface service in response to the request. The API is also configured to extract data from data repositories in the vendor inventory management system.

In another aspect of the invention, a count sheet is created by the sterile processing information system. The count sheet comprises a barcode for each of the third party assets identified in the third party asset data, and each barcode is associated with the instructions for use and a product description for a third party asset. One or more bar code scanners are communicatively connected to the sterile processing information system, and the sterile processing information system receives bar code scan inputs of the count sheet to document and verify hospital receipt of the third party assets into the hospital. The sterile processing information system also receives bar code scan inputs of the count sheet to document sterilization of the third party assets and verify that the sterilization settings of the sterilizer match the sterilization requirements of the respective third party assets.

This physical count sheet and the electronic record in the sterile processing information system which mirrors the printed physical count sheet, with the data derived directly from the parsable or structured data retrieved from the vendor loaner system, follows the loaner set throughout its cycle at the hospital. The data from this physical count sheet, as well as the data from the electronic record in the sterile processing system from which it was produced, enables the hospital to manage processes for documenting usage, charging, and restocking of consumable items from the loaner set.

Other advantages and features of the invention will be apparent to those skilled in the art after reviewing the figures and the following description as well as the appended claims.

BRIEF DESCRIPTION OF THE DRAWINGS

FIG. 7 depicts an exemplary embodiment of a count sheet.

FIGS. 11A and 11B depict exemplary embodiments of instrument trays of a loaner set.

FIGS. 12A-12E depict exemplary screen shots of a sterile processing information system handling hospital owned instrumentation.

FIGS. 13A-13C depict exemplary screenshots of a sterile processing information system handling a loaner set.

Figure 14A:
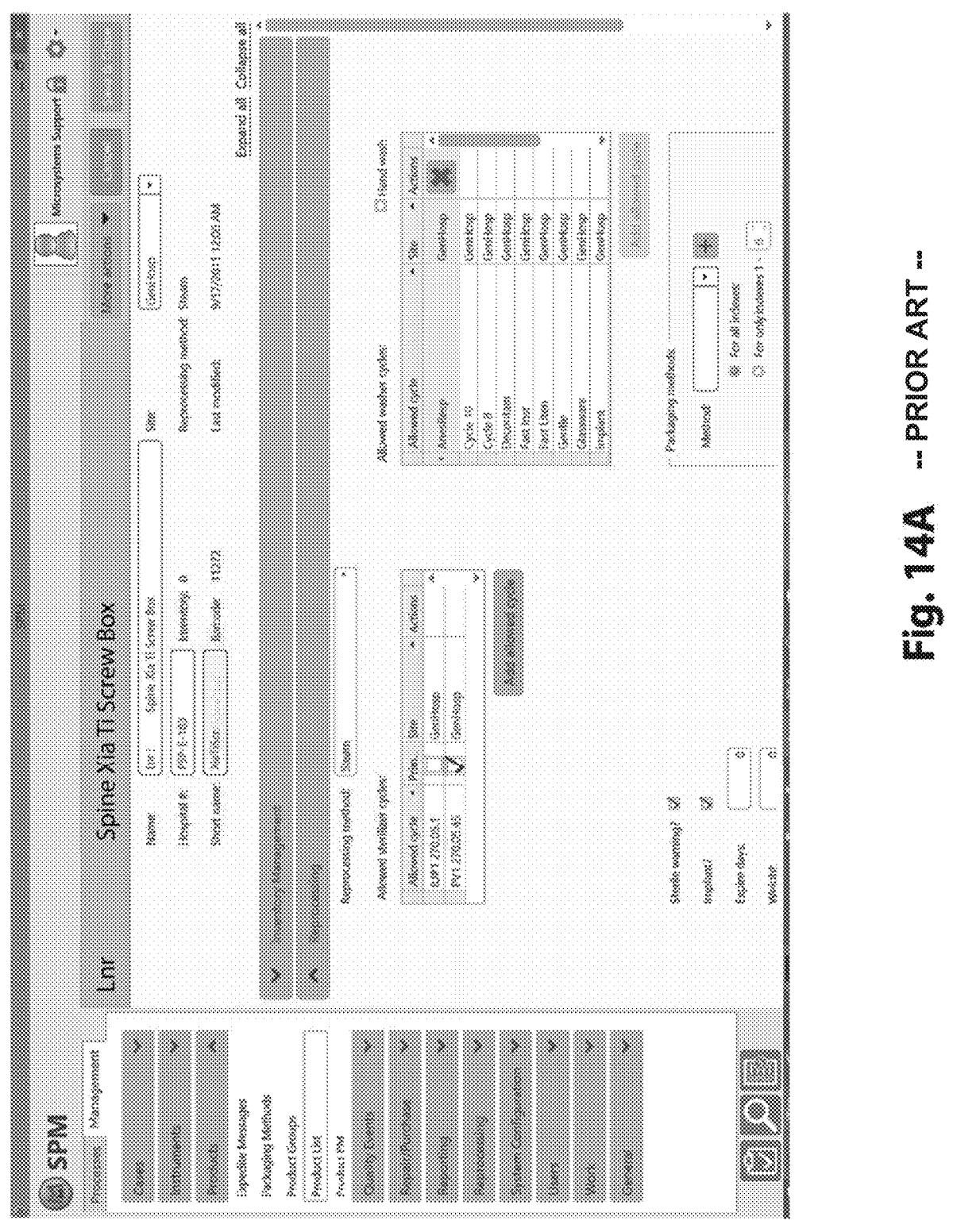
Figure 14B:
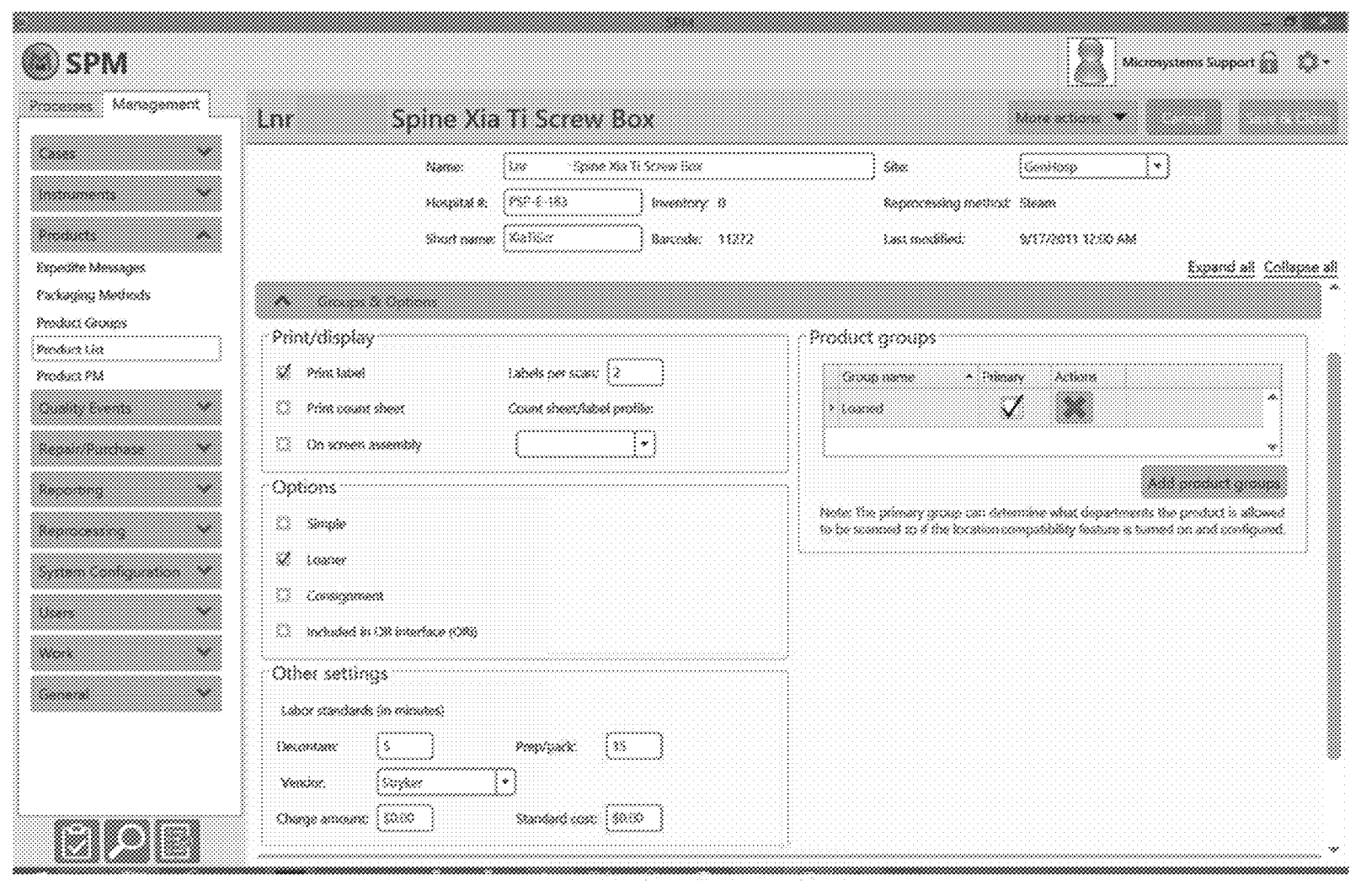

FIGS. 14A and 14B depict exemplary screenshots of a sterile processing information system loaner set description.

DETAILED DESCRIPTION

Figure 1:
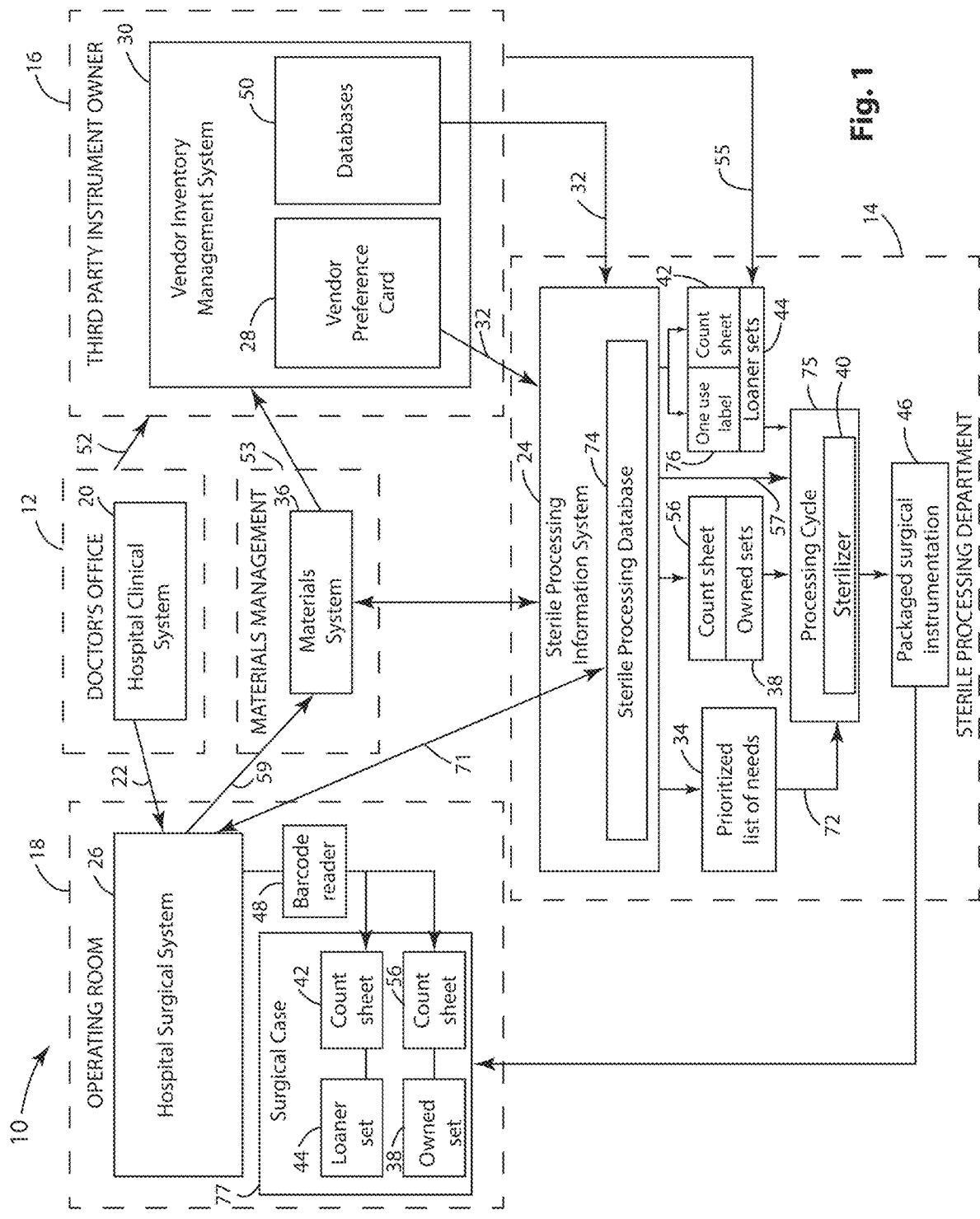
FIG. 1 is a system diagram of an exemplary embodiment of an instrumentation management system.

FIG. 1 is a system diagram that depicts an exemplary instrument management system 10 for implementing the invention. The exemplary instrument management system 10 connects a doctor's office 12, a sterile processing department (SPD) 14 in a hospital, a third party instrument owner 16, the hospital's materials management department 53, and the operating room 18 to schedule, acquire, and manage surgical instrumentation, including implants and/or consumables required for surgery.

In the doctor's office 12, one or more physicians use a hospital clinical system 20 to schedule a surgery. The hospital clinical system 20 may be a hospital records and scheduling system as provided for example by Cerner Corporation or Epic Systems Corporation. The hospital clinical system 20 creates a hospital preference card that includes information needed to schedule and prepare for a surgery. The hospital preference card identifies the needed operating room or rooms, personnel required for the surgery, as well as instrumentation and consumables required for the surgery. In the case of the instrumentation and consumables, the hospital preference card may specifically identify all of the hospital owned assets, including instruments and instrument sets, and/or consumables, but may merely include an identification that additional instrumentation or consumables provided by a third party are required. Communication 22 between the hospital clinical system 20 and the hospital surgical system 26 provides the hospital preference card to the hospital surgical system 26 which schedules the rooms, personnel, and other aspects of the surgery. The hospital clinical system 20 and hospital surgical system 26 may be part of the same commercial information system, although the hospital clinical system 20 and hospital surgical system 26 may be separate commercial systems communicating electronically to each other.

Communication 71 between the surgical system 26 and a sterile processing information system 24 in the SPD 14 can be provided for example by the ORi interface software available from Material Management Microsystems, Inc. This communication 71 provides the hospital preference card to the sterile processing information system 24. The sterile processing information system 24 also receives a bill of known materials as will be discussed in further detail herein, but which typically will represent only the hospital-owned instrument sets. The bill of materials will exemplarily be provided to the sterile processing information system for use in the instrument set recipe described above with respect to FIGS. 12A-12E. The communication 71 to the sterile processing information system 24 includes the hospital preference card and scheduling information related to the case, for example case number, physician, operating room, and start/end time. In an exemplary embodiment, all of this information is provided to the SPD staff through the sterile processing information system as depicted in FIGS. 12A-12E.

Figure 8A:
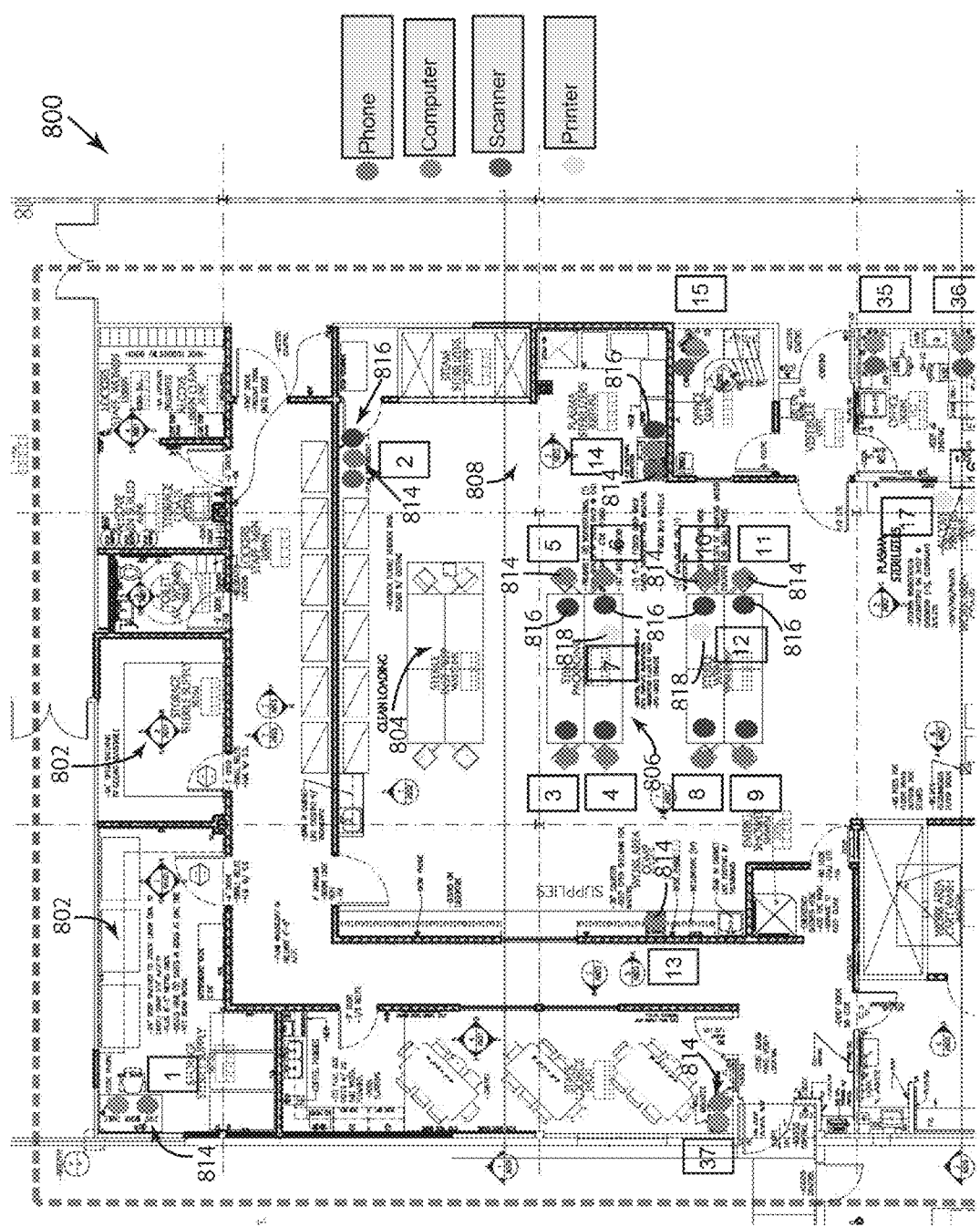
FIGS. 8A and 8B depict a schematic diagram of an exemplary embodiment of a sterile processing department (SPD).
Figure 8B:
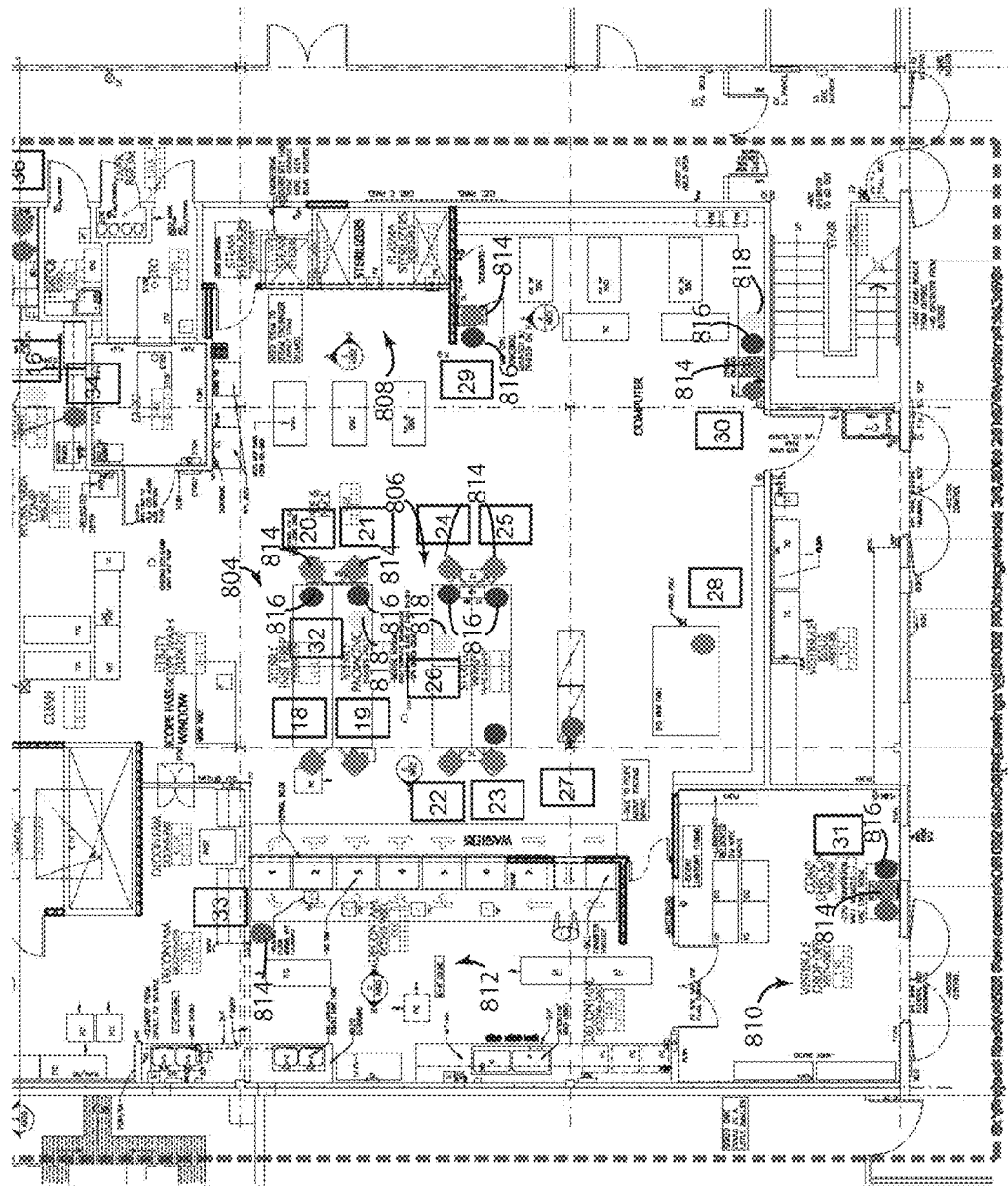

The sterile processing information system 24 is typically embodied on a network of computers located throughout the sterile processing department 14, and as generally depicted in the schematic diagram of FIGS. 8A and 8B. While described in further detail herein, the sterile processing department handles the cleaning, inspection/assembly, packaging, and sterilizing of owned sets and loaner sets to prepare them for use in surgery. Each of these tasks may be performed by SPD personnel at designated work stations within the SPD as depicted in FIGS. 8A and 8B. Exemplarily each of these work stations include at least one computer terminal to access the sterile processing information system and at least one barcode or other input scanner for use as described herein. Referring back to FIG. 1, the sterile processing information system 24, operating on one or more computers associated with each of these tasks, schedules and documents the performance of each of these tasks for each owned set and loaner set in the manners as described in further detail herein.

If a third party vendor 16 is used to obtain an implant and specialized loaner sets of instrumentation are needed, the surgeon 12 may request the implant and/or loaner sets with a vendor preference card 28, which may be maintained and managed by the third party vendor 16 or by a service managing vendor set loaner data and preference card information for the third party instrument owner. In an exemplary embodiment, the vendor preference card 28 is established based upon communication 52 between the surgeon and vendor. It will be recognized that in other embodiments at least some of the communication may be between the surgeon and another third party representing the vendor or providing communication with the vendor. The vendor preference card 28 specifies the implant or implants and any other consumables needed or requested along with the particular instrumentation to be provided in the loaner sets. In some embodiments, the vendor may specify some or all of the instruments in the loaner sets based upon the implant or consumable selected by the surgeon. The vendor preference card 28 information may be embodied at the doctor's office 12 or with the third party instrument owner 16 (or service), but the information contained in the vendor preference card 28 is exemplarily stored within a vendor inventory management system 30 owned by, or operated on behalf of, the third party instrument owner 16. It is understood that the vendor inventory management system 30 may be an inventory system or software owned and operated by the third party instrument owner or may be another vendor through which the third party instrument owner contracts for inventory management. The vendor preference card 28 may include referential information about the surgical case as stored in the hospital clinical system 20 and the hospital surgical system 26, where such referential information may include a case number, a surgeon, and a surgery date and/or time.

In the embodiment shown in FIG. 1, the third party instrument owner 16 or the operator of the vendor inventory management system 30 maintains databases 50 that are likely to include, but not limited to, identifications of all vendor owned assets, and loaner sets, content of loaner sets, IFU's, pictures, and vendor owned asset documentation.

Since the vendor inventory management system 30 contains the vendor preference card 28, the third party instrument owner, or the third party manager for the instrument owner is in possession of information representative of the implant and instrumentation that must be incorporated with information representative of the hospital owned assets necessary to complete documentation and sterile processing requirements placed upon the hospital for all of the instruments and consumables.

The sterile processing information system 24, which may exemplarily include features of the SPM system available from Materials Management Microsystems, communicates with the vendor inventory management system 30 to obtain vendor loaner set data 32. The loaner set data 32 includes the list of all loaner sets specified in the vendor preference card 28, plus additional information described below stored in the databases 50. The vendor loaner set data 32 is desirably transferred in parsable files, preferably as structured data files or messages containing information related to the surgical case, the vendor and vendor representative, and the loaner sets specified in the vendor preference card 28 along with their related loaner set data. As an example, the parsable files can be structured in a JSON structured data format, in an XML structured data format; or in an HL7 structured data format. Other types of parsable data formats can be used to implement the invention such as delimited data files, but are not preferred. The vendor loaner set data 32 is pushed to or retrieved by the sterile processing information system 24 in real-time as vendor preference cards 28 are finalized, or at periodic intervals, to capture any new vendor loaner set data 32 as provided by new or updated vendor preference cards 28 in the vendor inventory management system 30. In some embodiments, this information may be exchanged, e.g., every 30 or 90 seconds, including other intervals as may be recognized, including less frequent intervals. In an alternative embodiment, the sterile processing information system 24 accesses the databases 50 of loaned asset information directly to retrieve and/or confirm the most up to date loaner set data 32 prior to scheduling and/or other processing as described herein by the sterile processing information system 24.

The vendor loaner set data 32 obtained from the vendor inventory management system 30 may include an identification of all of the instruments, instrument sets, and consumables, including implants, to be provided by the vendor. The vendor loaner set data may further include background information, photographs of the instruments and/or consumables, and IFUs for the instruments and consumables, including sterilization instructions, which may include special sterilization instructions beyond standard sterilization processes. In some cases, this information is provided as the vendor loaner set data 32 from the vendor inventory management system 30. In other cases, some or all of this information is accumulated in the sterile processing information system 24, or is provided by reference to one or more external databases.

Current solutions focus on managing the hospital-owned assets or the vendor-provided assets. Such current solutions operated in and by the hospital will manage the hospital-owned assets, whereas such current solutions operated for non-hospital entities such as the doctor or vendor will manage the vendor-provided assets; each solution is parochial in its focus. The invention transmits parsable or structured data to provide a unified presentation of all i, instrument sets, and consumable assets required for the upcoming cases. The structured or parsable data includes data which allows the sterile processing information system 24 to unite the vendor preference card 28 and vendor loaner set data 32 with the surgical case 71 from the surgery system 26 by a unique case identifier, e.g., the case ID or case number. The structured or parsable data also includes data which allows the sterile processing information system 24 to either create a fully or largely populated record of that loaner set in the sterile processing information system 24, or to match the loaner set data 32 with a known record in the sterile processing system 24. Should a new loaner set record need to be created, the structured or parsable data enables population of the fields in the loaner set data in the sterile processing information system 24, such that the sterile processing department 14 knows the manufacturer's IFU for properly cleaning and sterilizing the equipment as described below.

In order to integrate the loaner sets into an effective and efficient operation of the sterile processing department through the sterile processing information system 24, the vendor loaner data 32 must be integrated into the sterile processing information system. While the vendor loaner set data may include a wide variety of information, that information related to the identification of the contents of the loaner set as well as the most important information needed for the sterile processing of the loaner set are most important. For example, the information identified in the screen shots 12A-12E as available for possible owned assets is desired for each of the loaner sets. This not only includes the recipe or contents of the loaner set, but the sterilization instruction, including, e.g., the reprocessing method, allowed sterilizers cycles, allowed washer cycles, packaging methods, and an indication of whether or not an implant exists in the loaner set. While all of this information may be found in the formal instructions for use (IFU), the IFU is typically a large single document that includes far more information than just the information identified above. The formal IFU document is important for the SPD to have on hand and available should it need to be referenced, but may often be an unwieldy document from which to directly obtain the processing information. As such, it is advantageous for the loaner set identification information, loaner set content, and reprocessing instruction be made available in one or more structured or parsable data files for incorporation into the sterile processing information system 24.

In some embodiments, the vendor loaner set data may be categorized for example as loaner details data which includes a case identification number, a vendor identification number, the formal instructions for use document and an identification of each of the loaner sets. Other vendor loaner set data is categorized as loaner content data which includes the recipe for each of the identified loaner sets and further may include the reprocessing instructions for each of the identified loaner sets. Alternatively, all of the loaner details data and the loaner content data can be transmitted together, for example, in a parsable or structured data format. Updates to the data may be made periodically.

Desirably, a hierarchical data structure is used to communicate the parsable data. For example, the case identification number and vendor identification number are representative data elements of the root data element. The loaner set identifications of each loaner set that is provided to support the surgical case constitutes child data elements underneath the root data element, such that each loaner set that is included is associated with the root surgical case for which it will be delivered. It is expected that multiple loaner sets will often be associated with the root data element of the surgical case and the vendor providing loaned assets for the case. Extending this example, it is expected that child data elements for each loaner set data element will exist to provide the "recipe", or list of contents, that will be included in each loaner set data element. This recipe consists of child data elements representing the instruments, implants and/or consumables that comprise each loaner set. Given that data elements from any part of the hierarchical data structure may change over time, for instance when the recipe for a loaner set is modified in the vendor inventory management system 30, when the sterile processing information system 24 requests data from the vendor inventory management system 30, each data element in the hierarchical data structure will need to be examined by the sterile processing information system 24 and updated as necessary in the sterile processing database 74.

In a still further embodiment, the hierarchical structured data concept may be further extended to include the reference files, IFU, and/or pictures for each loaner set that will be provided for any given surgical case. For example, the important reprocessing instructions for one or more loaner content files may be included as child data for each loaner set, along with pictures, hyperlinks to online content, IFU, or other materials. Such an embodiment promotes basic integration of the vendor loaner set data into the sterile processing information system 24, and separates the data into components which can be accessed and integrated independently of each other. As mentioned, the parsable or structured data for the loaner set detail will include the contents of each loaner set, which may include instruments and/or consumables. In addition to having specific IFU and cleaning and sterilization instructions similar to instruments, information relative to consumables in the parsable or structured data may include information such as lot number and manufacturer information. Further if, the formal instructions for use (IFU) document is provided in a standardized, included, or template form, the instructions for use document may be processed for example with text recognition, natural language search, and/or physiologic and/or machine learning to be processed for extraction of the reprocessing instructions and other vendor loaner set data directly from the formal instructions for use.

Figure 1A:
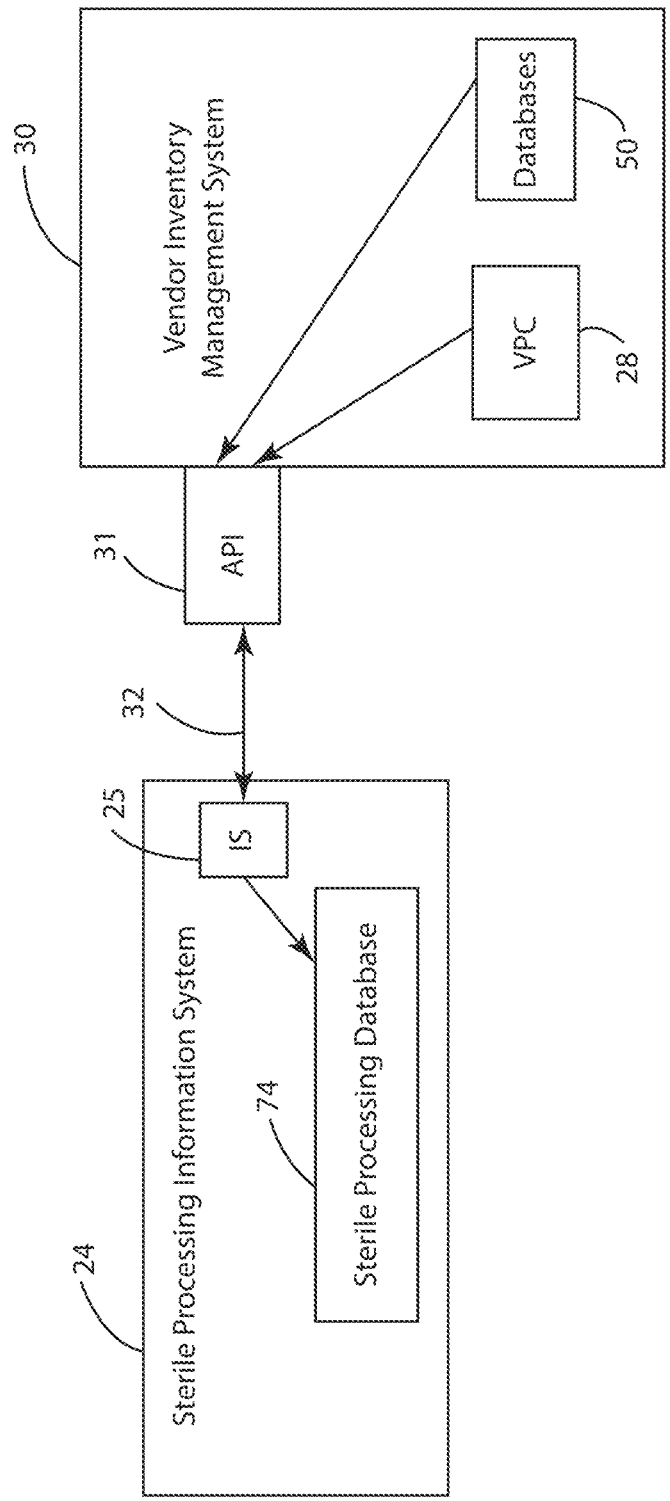
FIG. 1A is a diagram of a communications interface between a sterile processing information system and a vendor inventory management system configured in accordance with an exemplary embodiment of the invention.

FIG. 1A illustrates one means for the sterile processing information system 24 to obtain structured data 32 from the vendor inventory management system 30. Data may be stored in the vendor databases 50 with one data repository for surgical cases, another for vendors, another for vendor representatives, another for loaner sets available for distribution by that vendor and/or representative, another for the contents or recipe which make up each loaner set, and yet another for reference materials such as manufacturer IFU, pictures, videos or other documents for assisting in proper processing and handling of the loaner sets. The vendor inventory management system 30 exposes an application program interface (API) 31 to enable the sterile processing information system 24 to request data from the vendor inventory management system 30. More specifically, the sterile processing information system 24 includes an interface service 25 that periodically requests the API 31 for data. The API 31 may be a web service that the vendor inventory management system 30 exposes and which the interface service 31 recognizes and is able to request and receive structured data 32. The interface service 25 in the sterile processing information system 24 makes a request via the API 31 to retrieve structured data 32 for any upcoming surgical cases that have been identified in the vendor inventory management system 30 and in support of which vendor representatives have made commitments to provide loaner sets. Such a request is received by the vendor management inventory 30 system, which then returns the requested data 32 in a parsable or structured data format, such as JSON, XML, or HL7. One such example of an XML file might look as follows:

```
<ScheduledCases>
   <CaseDetail>
      <CaseNumber>12345</CaseNumber>
      <StartDateTime>2016-09-01 07:00:00</StartDateTime>
      <EndDateTime>2016-09-01 09:00:00</StartDateTime>
      <Vendor>VendorA</Vendor>
      <VendorRepName>Jones, Alex</VendorRepName>
      <ExpectedDeliveryTime>2016-08-31 07:00:00</ExpectedDeliveryTime>
      <LoanerSets>
         <LoanerSet>
            <Id>100</Id>
            <Name>Loaner Instrument Set 1</Name>
            <Quantity>1</Quantity>
            <ContainsImplantables>False</ContainsImplantables>
            <SterilizationMethod>
               <Name>Steam</Name>
               <Process>PreVac</Process>
               <ExposureTime>10</ExposureTime>
               <ExposureTemp>270</ExposureTemp>
               <DryTime>45</DryTime>
            </SterilizationMethod>
            <PackagingMethod>
               <Name>Large Container</Name>
               <Instructions>Place both trays of instruments in Large Container, include filters, and seal for sterilization</Instructions>
            </PackagingMethod>
            <ReferenceFiles>
               <FilePath>http://www.somesite.com/file1-1.pdf</FilePath>
               <FilePath>http://www.somesite.com/file1-2.pdf</FilePath>
            </ReferenceFiles>
            <LoanerSetContents>
               <LoanerContentItem>
                  <Id>1</Id>
                  <Name>Clamp, Babcock, Straight, 6 inch</Name>
                  <Manufacturer>Inst Manufacturer 1</Manufacturer >
                  <ProductNumber>11-111</ProductNumber>
                  <Quantity>2</Quantity>
                  <Consumable>False</Consumable>
                  <LotNumber />
                  <SterilizationMethod>Steam</SterilizationMethod>
               </LoanerContentItem>
               <LoanerContentItem>
                  <Id>2</Id>
                  <Name>Clamp, Babcock, Straight, 8 inch</Name>
                  <Manufacturer>Inst Manufacturer 1</Manufacturer >
                  <ProductNumber>11-222</ProductNumber>
                  <Quantity>2</Quantity>
                  <Consumable>False</Consumable>
                  <LotNumber />
                  <SterilizationMethod>Steam</SterilizationMethod>
               </LoanerContentItem>
               <LoanerContentItem>
                  <Id>3</Id>
                  <Name>Clamp, Babcock, Curved, 6 inch</Name>
                  <Manufacturer>Inst Manufacturer 1</Manufacturer >
                  <ProductNumber>11-333</ProductNumber>
                  <Quantity>2</Quantity>
                  <Consumable>False</Consumable>
                  <LotNumber />
                  <SterilizationMethod>Steam</SterilizationMethod>
               </LoanerContentItem>
            </LoanerSetContents>
         </LoanerSet>
         <LoanerSet>
            <Id>101</Id>
            <Name>Loaner Implant Set 2</Name>
            <Quantity>1</Quantity>
            <ContainsImplantables>TrueContainsImplantables>
            <PackagingMethod>
               <Name>Small Container</Name>
               <Instructions>Place basket of implants in Small Container, include filters, and seal for sterilization</Instructions>
            </PackagingMethod>
            <SterilizationMethod>
               <Name>Steam</Name>
               <Process>PreVac</Process>
               <ExposureTime>12</ExposureTime>
               <ExposureTemp>270</ExposureTemp>
               <DryTime>45</DryTime>
            </SterilizationMethod>
            <ReferenceFiles>
               <FilePath>http://www.somesite.com/file2-1.pdf</FilePath>
               <FilePath>http://www.somesite.com/file2-2.pdf</FilePath>
            </ReferenceFiles>
            <LoanerSetContents>
               <LoanerContentItem>
                  <Id>4</Id>
                  <Name>Plate, Large, 8-hole</Name>
                  <Manufacturer>Implant Manufacturer 1</Manufacturer >
                  <ProductNumber>22-111</ProductNumber>
                  <Quantity>2</Quantity>
                  <Consumable>True</Consumable>
                  <LotNumber>ABC-111</LotNumber>
                  <SterilizationMethod>Steam</SterilizationMethod>
               </LoanerContentItem>
               <LoanerContentItem>
                  <Id>5</Id>
                  <Name>Plate, Large, 6-hole</Name>
                  <Manufacturer>Implant Manufacturer 1</Manufacturer >
                  <ProductNumber>22-222</ProductNumber>
                  <Quantity>1</Quantity>
                  <Consumable>True</Consumable>
                  <LotNumber>ABC-222</LotNumber>
                  <SterilizationMethod>Steam</SterilizationMethod>
               </LoanerContentItem>
               <LoanerContentItem>
                  <Id>6</Id>
                  <Name>Plate, Small, 6-hole</Name>
                  <Manufacturer>Implant Manufacturer 1</Manufacturer >
                  <ProductNumber>22-333</ProductNumber>
                  <Quantity>2</Quantity>
                  <Consumable>True</Consumable>
                  <LotNumber>ABC-333</LotNumber>
                  <SterilizationMethod>Steam</SterilizationMethod>
               </LoanerContentItem>
            </LoanerSetContents>
         </LoanerSet>
      </LoanerSets>
   </CaseDetail>
</ScheduledCases>
```

The specific format of the data may vary, and retrievable content may vary based on the vendor inventory management system 30. However, this basic content is extracted when interface service 25 of the sterile processing information system 24 requests the data 32 from the vendor inventory management system 30 via the API 31; and the extracted data is formatted in an agreed upon format that is parsable or structured, readable by the interface service 25 and usable by the sterile processing information system 24.

The sterile processing information system 24 contains a large number of data repositories, e.g., 200-300, in the sterile processing database 74 for different categories of information. The interface service 25 processes the structured data file for the case upon receipt from the API 31, and writes the data to the appropriate data repository in the database 74. For example, upon receipt, data about the case is stored in a database repository for surgical cases, including the case number, the unique identifier which links the case from the vendor management system with the surgical case record from the hospital surgery system. Additionally, the interface service 25 stores a record for the loaner "order" which includes information about which vendor and vendor representative has committed to delivering loaner assets for this surgical case, and when the expected delivery of those assets is. Finally, the interface service 25 parses the information about each loaner set that will be delivered as part of this process. Using the ID provided by the vendor inventory management system 30 for the loaner set, the sterile processing information system 24 will determine if this loaner set has already been identified within the sterile processing information system 24. If it has not been previously identified, a process desirably exists to review this item and to approve of the creation of a "known" asset record in the sterile processing information system 24. This process then creates a link between all future receipts of this loaner set ID by the sterile processing information system 24, and validates that all information provided by the vendor inventory management system 30 is properly imported into the sterile processing information system 24 and that all required information is present. In a similar manner, the contents for the loaner set are checked against "known" content items in the sterile processing information system 24, and new content items are created as necessary to create the complete recipe or contents list in the sterile processing information system 24. Additional detail about the loaner set, such as if the loaner set contains implantable items, processing instructions, sterilization methodologies, and all reference files provided by the loaner set data are included in the "known" asset record. If, on the other hand, the ID provided by the vendor inventory management system 30 for this loaner set has already been previously identified, the sterile processing information system 24 may simply link this loaner set for the case with the already identified known asset record. Regardless, once the loaner set has been identified with a known asset in the sterile processing information system 24, this known asset is then identified as a loaner set that will be brought by the vendor in support of the respective surgical case.

Referring again to FIG. 1, one challenge is to marry the vendor loaner set data with the hospital owned assets identified on the hospital preference card 22 into a particular surgery to be performed such that the loaner sets and consumables may be eventually integrated with the hospital owned assets and packaged for delivery to the operating room. The sterile processing information system 24 may use information provided in the vendor loaner set data 32 to associate the vendor loaner set data with a forthcoming surgical case. For example, the vendor loaner set data 32 may contain the case number for an upcoming surgical case, which can be used to associate the vendor loaner set data 32 with the surgical case information 71 transmitted by the hospital surgical system 26 to the sterile processing information system 24. Other data that may be associated between data sources can be identification of a surgeon, or other staff personnel assigned to a surgery an expected delivery time of the loaner set by the vendor, and/or an analysis of the instruments and/or consumables identified in the vendor loaner set data. Upon this determination, the vendor loaner set data is appended to the hospital preference card so that the sterile processing information system 24 can present a full picture of the featured demands on the sterile processing department 14 to prepare all hospital owned assets and loaner sets for the scheduled surgery. By having the complete information for all of the instruments and consumables regardless of the ownership of the instruments or consumables, the sterile processing information system 24 can produce a prioritized list of needs 34 that embodies and schedules all of the processes and resources needed to prepare the owned sets and the loans sets for surgery. The sterile processing department can mobilize resources, staff, and production/sterilization capacity to meet the internal service levels and inventory fill rates of the operating room based upon the prioritized list of needs 34. Efficient and effective internal processing of sterile instrumentation has many operational, financial, and clinical risk-management advantages.

For example, the sterile processing information system 24 contains a sterile processing database 74, from which it identifies requested instrument sets identified in the hospital preference card for a surgery. The sterile processing database 74, as mentioned, contains many data repositories including, e.g., a data repository for hospital-owned instrument inventory, one for surgical cases, one for vendor representative information, one for loaned assets on hand, etc. . . . . The sterile processing database 74 also maintains up-to-date information regarding the billing information and sterilization requirements for such instrument kits. Additionally, the sterile processing information system 24 synchronizes its database of instruments, implants and consumables with the hospital materials system 36 so that charge information for all chargeable contents of an instrument set are available in both the sterile processing information system 24 and the materials system 36. The sterile processing information system 24 further contains all contents (instruments, implants, consumables, etc.) that make up an instrument set. In an embodiment, the material system 36 includes a database of instruments and consumables that includes identification of each of these assets and charge information therefor. In the case of third party owned assets, the identification and charge information enables coordination of documenting asset use and appropriate billing. The materials system 36 also operates to facilitate ordering and purchasing of assets, including third party owned assets provided to the hospital on consignment. With this identification of instrument set contents, personnel in the sterile processing department 14 can assemble the hospital owned assets 38 into the required instrument kits. Further reference to the sterile processing database 74 identifies required sterilization processes including a type of sterilization, length of sterilization time, sterilizer settings, and post sterilization purification requirements for the approved use of the instruments. As indicated above, this information (contents of loaner sets, sterilization instructions, IFUs) is similarly provided with or by reference to the vendor loaner set data 32. Personnel in the sterile processing department 14 use the loaner set contents and IFUs to properly assemble and package the loaner instrument sets 44. With reference to provided sterilization instructions, a sterilizer 40 can be operated to sterilize batches of instrumentation having the same sterilization requirements such that the sterilizers 40 are operated at an optimal capacity and operation rate promoting efficiency in the sterile processing department. Sterilization instructions available for both hospital-owned sets 38 and vendor-owned loaner sets 44 allow sterile processing department personnel to sterilize both types of sets according to their specific requirements.

Figure 9:
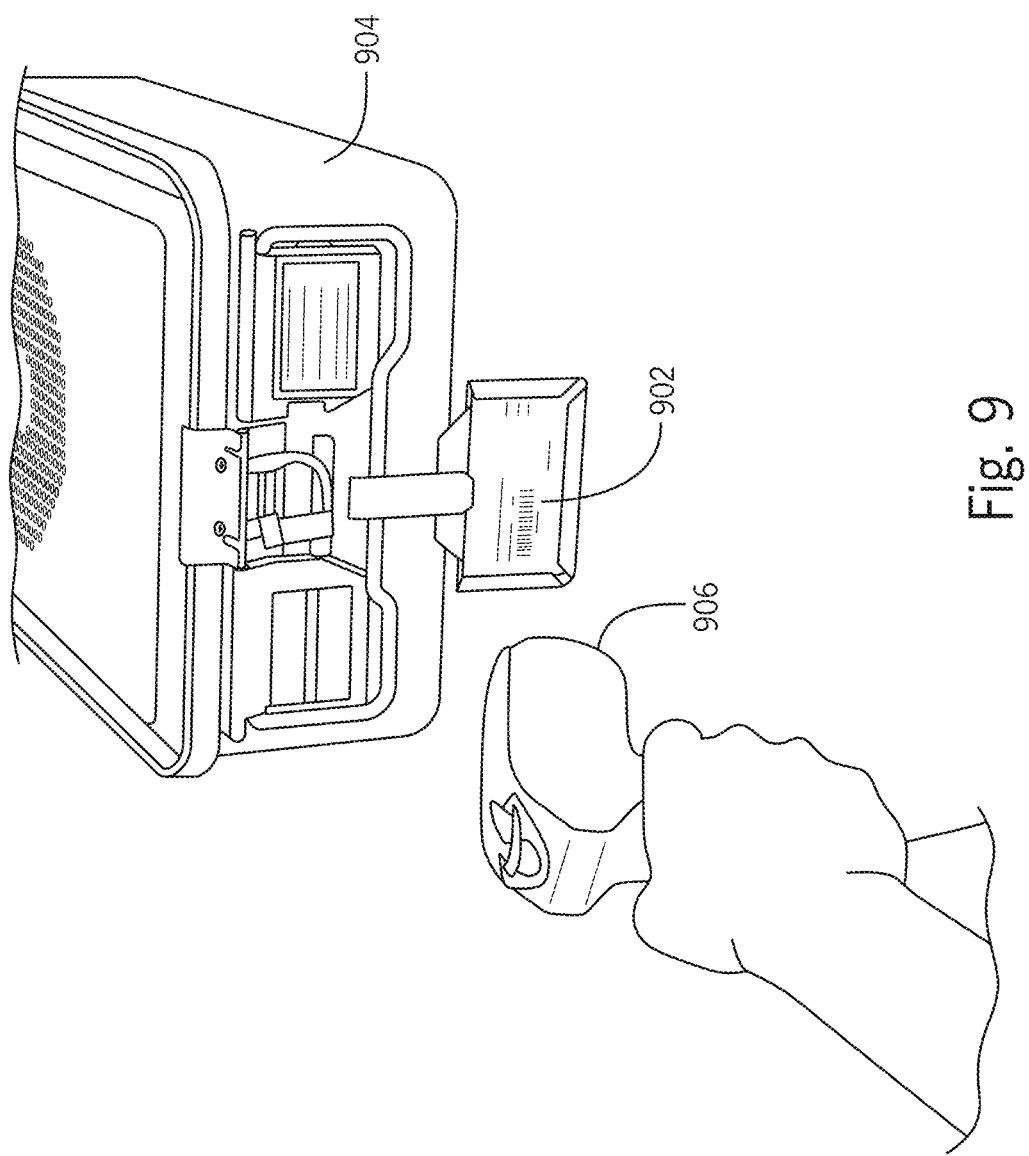
FIG. 9 depicts an exemplary embodiment of a one-use barcode being scanned.
Figure 10:
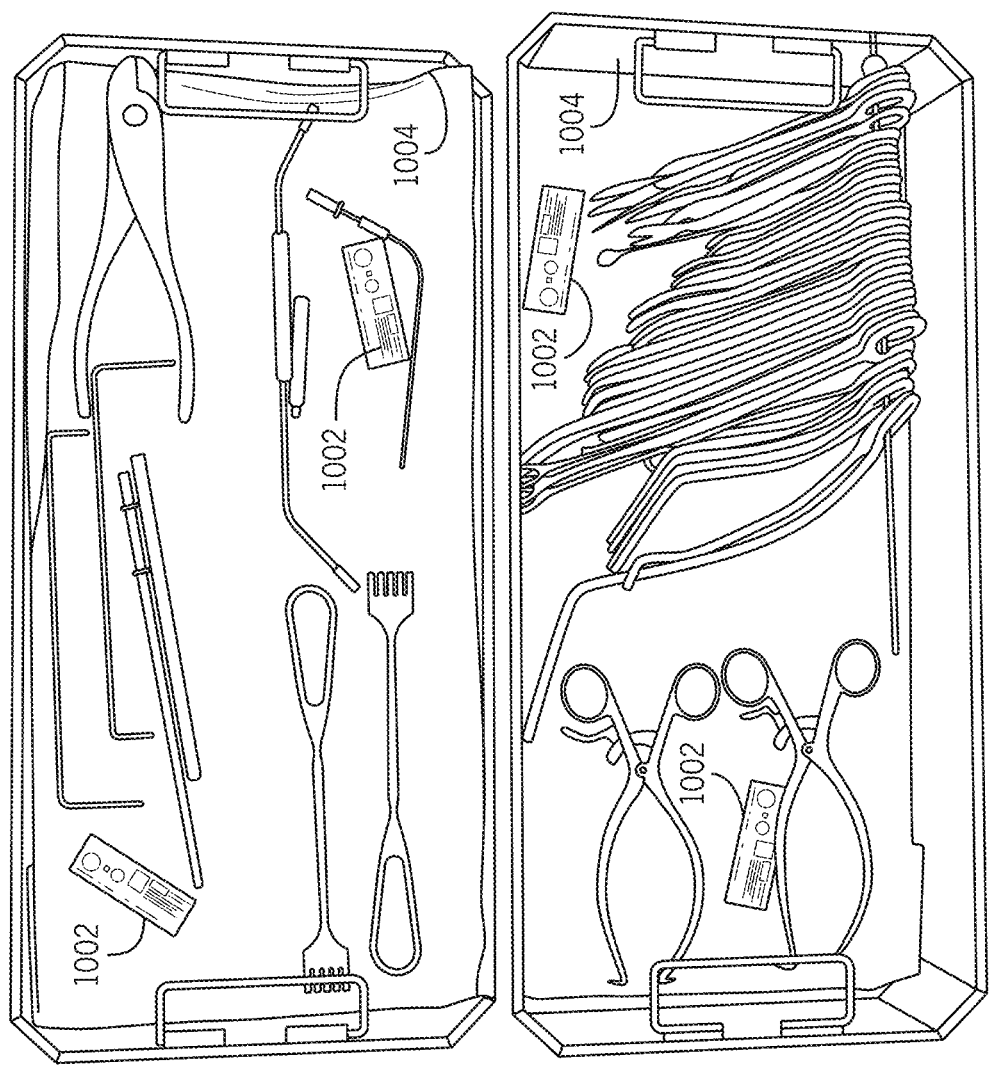
FIG. 10 depicts an exemplary embodiment of instrument sets including at least one one-use barcode.

The hospital owned assets 38 may individually include identification barcodes, or barcodes assigned to the instrument set of hospital owned assets. The barcodes are scanned prior to loading the instruments in a sterilization cycle in the sterilizer 40 to verify the sterilization requirements between the instruments and the settings of sterilizer 40. FIG. 9 depicts an exemplary embodiment of a barcode 902 associated with an instrument set 904 and configured to be scanned by a barcode scanner 906. FIG. 10 depicts an exemplary embodiment of barcodes 1002 associated with an instrument tray 1004 and configured to be scanned by a barcode scanner (not depicted).

Loaner sets 44 are delivered by the third party instrument owner 16 to the sterile processing department 14. Upon receiving the loaner sets 44, sterile processing personnel match the received loaner sets 44 with the loaner sets identified in the loaner set data communicated at 32 to the sterile processing information system 14. In this process, each loaner set 44 is identified, along with vendor, delivery time, and case information such as scheduled start time and case location and physician. To physically incorporate the loaner sets into the sterile processing information system 24, the sterile processing information system 24 takes two actions. The sterile processing information system 24 produces a one-use barcode label 76 to uniquely track each loaner set throughout the reprocessing cycle 75 and delivery 73 to the surgical case 77. The one-use barcode label 76 exemplarily embodies an identification of the instrument/consumable set and any IFU associated with that set. The sterile processing information system further produces a count sheet 42 listing all of the instruments and consumables (including implants) to be provided by the vendor in each loaner set 44. The count sheet 42 may be a physical sheet produced by the sterile processing information system 24 which includes a barcode associated with each of the instruments and consumables in the loaner set 44. In an embodiment as described in further detail herein, the barcodes embody an identification of the instrument and/or consumable, and charge information therefore, which has been derived from the parsable or structured data 32 retrieved from the vendor inventory management system 30. It is recognized that other information may also be incorporated into the bar code. In an embodiment, the barcode is a 2-D barcode. In an exemplary embodiment, the count sheet is printed from a printer communicatively connected to the sterile processing information system 24. As described below, this physical count sheet and the electronic record in the sterile processing system which mirrors the printed physical count sheet, with the data derived directly from the parsable data file retrieved from the vendor loaner system, follows the loaner set throughout its cycle at the hospital. The data from this physical count sheet, as well as the data from the electronic record in the sterile processing system from which it was produced, enables the hospital to manage processes for documenting usage, charging, and restocking of consumable items from the loaner set.

FIG. 11A exemplarily depicts a tray of instruments from a loaner set. FIG. 11B exemplarily depicts a plurality of consumables (e.g. cannulated screws) which may be provided in a caddy, tray or other case associated with the instrument tray depicted in FIG. 11A as part of the loaner set. FIG. 7 depicts an exemplary embodiment of a count sheet 700. The count sheet 700 is exemplarily the count sheet generated for use with the consumables as depicted in FIG. 11B. the count sheet 700 identifies each of the consumables (e.g. screws) that make up contents of that tray or caddy or portion of the loaner set. Each of the identified consumables is further associated with 2-D barcode as described above.

Upon receipt of the loaner sets 44 into the sterile processing department 14, the loaner sets 44 are examined and the barcodes presented in the count sheet 42 scanned upon verification that each of the instruments on the count sheet 42 were received as part of the loaner set. Therefore, in embodiment, receipt of the loaner sets 44 by the sterile processing department 14 is a verification process against the already produced count sheet 42 rather than an inventorying and initial documenting process to identify what has been received in the loaner set 44 in the first place. Upon this verification of receipt of the instruments, the loaner sets 44 may be processed according to the full prioritized list of needs 34 produced by the sterile processing information system. As noted above, the prioritized list of needs provides a schedule of work to process all hospital owned assets and third party assets for the surgeries to be performed that day. This processing includes cleaning, inspection/assembly, packaging, and sterilizing.

An advantage of embodiments disclosed herein, because the previously receipt of vendor loaner set data, the contents and reprocessing instructions for the instruments in the loaner sets are known before the loaner sets 44 are received by the sterile processing department 14. Because the sterile processing information system 24 already previously received the vendor loaner set data, the prioritized list of needs 34 could be created in advance to efficiently reprocess and sterilize the hospital owned instruments and consumables and the instruments and consumables received in the loaner sets 44. In embodiments, the sterilization and processing of the loaner sets 44 is incorporated with the processing and sterilization of the hospital owned assets. This is in contrast to previous systems whereby the contents of the loaner sets was unknown to the sterile processing information system 24 until the loaner set 44 were physically received and inventoried by the sterile processing department 14, and therefore, all of the sterilization processing of the loaner sets 44 had to be handled as a rush order upon receipt of the loaner set at the sterile processing department.

at least one count sheet 42 is specific to each of the loaner sets 44 and travels with the loaner set 44 through the rest of the instrument management system 10 as described in further detail herein. In an alternate embodiment, an electronic count sheet may be maintained in the sterile processing information system with the same information and barcodes as the printed count sheet. The one-use barcode label 76 additionally travels with the loaner set 44 through the rest of the instrument management system 10. During the reprocessing process (often as a part of packaging) if a physical count sheet 42 is used, the count sheet 42 is inside the packaging with the loaner set 44. With the count sheet 42 within the packaging, the one-use barcode label 76 on the outside of the packing is used to track and document the loaner set 44 within the system. Just prior to sterilization, the one-use barcode label 76 is then scanned with a barcode reader, for example scanning a barcode associated with the instrument set as a whole to verify the IFU and sterilization instructions for the loaner set with the settings and type of sterilizer 40. Upon this confirmation, the loaner set can be sterilized.

During the assembly, packaging and sterilization process, known as the reprocessing cycle 75, the sterile processing information system 24 alerts 57 sterile processing personnel of prioritization of needed hospital owned sets 38 and loaner sets 44. Additionally, during the reprocessing cycle 75, sterile processing personnel have continual reference 72 to the real-time prioritized list of needs 34 generated by the sterile processing information system 24. The prioritized list of needs 34 and the alerts 57 generated by the sterile processing information system 24 now capture the full bill of materials required for surgery, representing both the hospital preference card 22 and the vendor preference card 28 for the surgical case 77.

After sterilization, the sterilized hospital owned assets 38 and sterilized loaner sets 44 are grouped for delivery to the surgical case 77 location. The packaged, sterilized surgery instrumentation 46 includes the sterilized hospital owned assets and the sterilized loaner sets, the sterilized loaner sets including the count sheet 42 specific to that instrumentation set. In embodiments, the packaged surgery instrumentation 46 may undergo further sterilization depending upon the instrumentation itself and the sterilization requirements for the surgery.

The packaged surgical instrumentation 46 is transferred by the sterile processing department to the operating room 18 for use in the surgery.

In a still further aspect of embodiments as disclosed herein, during the surgery various instruments and/or consumables of the loaner set 44 may be used by the surgeon or other surgical personnel. In order to trace or track the use of tools and/or consumables from the loaner set, including implants, with the patient during the surgery, each instrument and consumable used must be documented in the hospital surgical system 26. In an embodiment, this documentation is facilitated by incorporation of a barcode scanner input device 48 to the hospital surgical system 26 and use of the barcode scanner 48 to scan the barcode assigned to each instrument of the loaner set on the count sheet 42 upon use of that instrument and/or consumable during the surgery. Scanning of the barcode on the count sheet can populate required fields in the hospital surgical system 26, exemplarily vendor identification, instrument or consumable identification code, instrument or consumable description, and expiration date, if applicable.

The hospital surgical system 26 can either store the implant and consumable usage documented through the barcode scanner 48 and/or can pass this information to the materials system 36, where charges are typically managed.

Finally, after the surgery is completed, the loaner sets can be repackaged for return to the vendor and the count sheets can be used a final time for verification and documentation that all of the instruments in the loaner set are returned back to the vendor. When the vendor replenishes the implants and consumables in the loaner sets, the vendor 16 will charge the hospital for implants and consumables used during the surgical case 77. Using the information captured by the hospital surgical system 26 via the barcode scanner 48, the hospital can verify the charges 70 made by the vendor.

Figure 2:
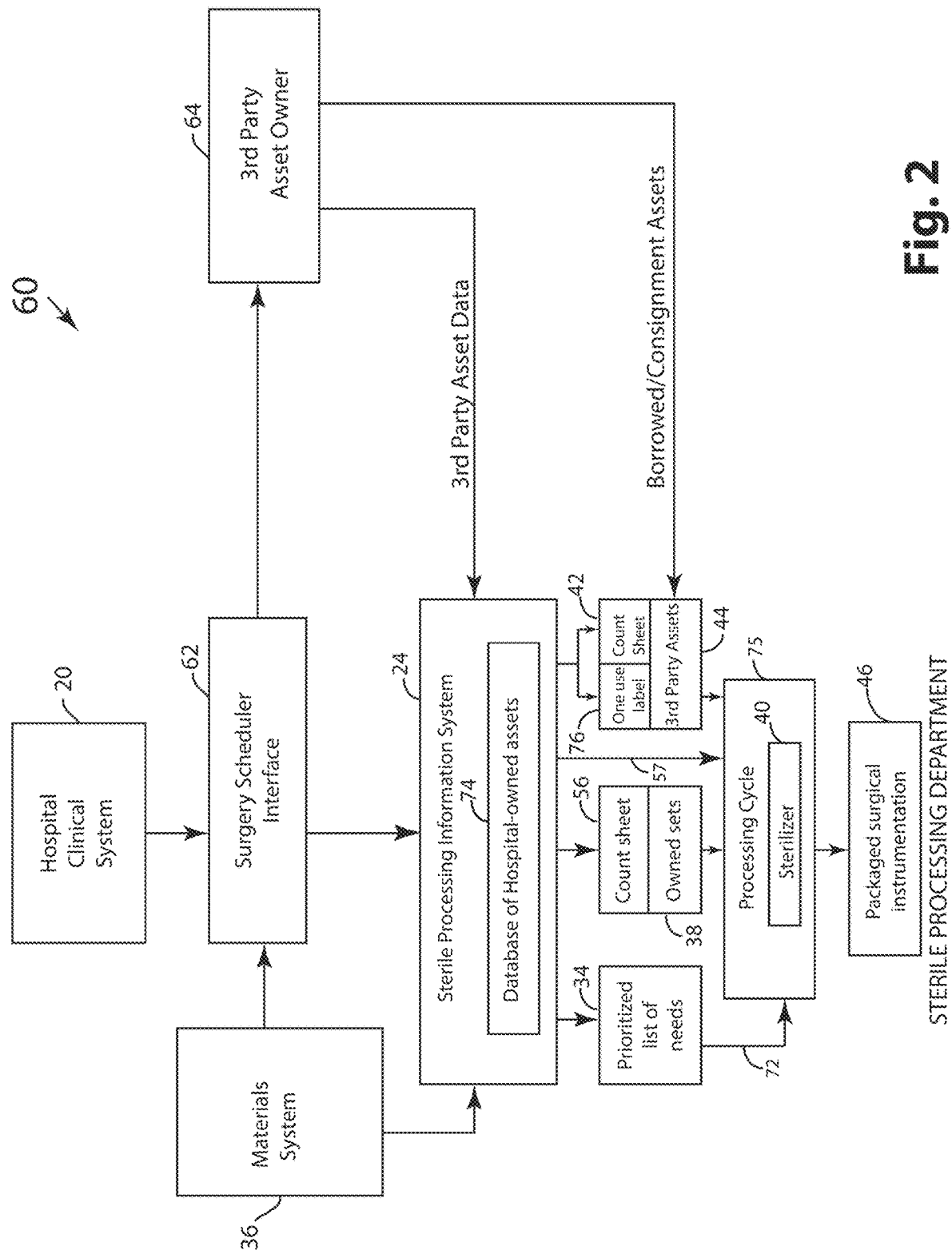
FIG. 2 is a system diagram of another exemplary embodiment of an instrumentation management system.

FIG. 2 depicts an alternative exemplary embodiment of an instrument management system 60, primarily depicting a manner in which an embodiment of the sterile processing information system 24 as disclosed herein may be used in connection with borrowed instrumentation or consignment supplies of implants or consumables. It will be recognized that like reference numerals are used to refer to like features between embodiments. In an exemplary embodiment, pins and/or screws may be provided by a vendor on consignment such that a wide variety of shapes and sizes of consumables (e.g. pins or screws) are available to the surgeon during the surgery and the hospital is billed for those consumables used from the tray when the vendor replenishes it.

In the exemplary embodiment 60, a surgery schedule interface 62 is in communicative connection with the hospital clinical system 20, the sterile processing information system 24, and the sterile processing database 74. The surgery schedule interface 62 facilitates producing the hospital preference card by providing naming conventions and descriptions consistent with the instruments and consumables to the preference card and verifies the instruments and consumables against actual available inventory levels of the hospital owned assets. If the surgery scheduling interface 62 identifies a conflict or an asset needed that cannot be met by hospital owned assets, then the surgery scheduling may facilitate communication with a third party asset owner 64 to arrange for assets to be borrowed from the third party asset owner. In an exemplary embodiment, the third party asset owner may be an affiliated hospital or may be another branch, office, or surgical unit of the same hospital, although one that keeps an inventory of hospital owned assets apart from the hospital owned asset typically handled by the sterile processing information system 24. The sterile processing information system 24 operates in a similar manner as described above and that it receives third party asset data from the third party asset owner to provide an indication of the borrowed assets. In an alternative embodiment, the surgery scheduling interface 62 may further provide the third party asset data to the sterile processing information system 24 by indicating the requested third party assets and confirmation that the third party asset owner will loan such assets to the hospital.

It will be understood that once the third party asset data is received by the sterile processing information system 24, the sterile processing information system can process and handle the borrowed assets and consigned assets in the manners as described above regarding the loaner instrument sets. The sterile processing information system 24 produces a count sheet 42 that is associated with the received third party assets 66.

Figure 3:
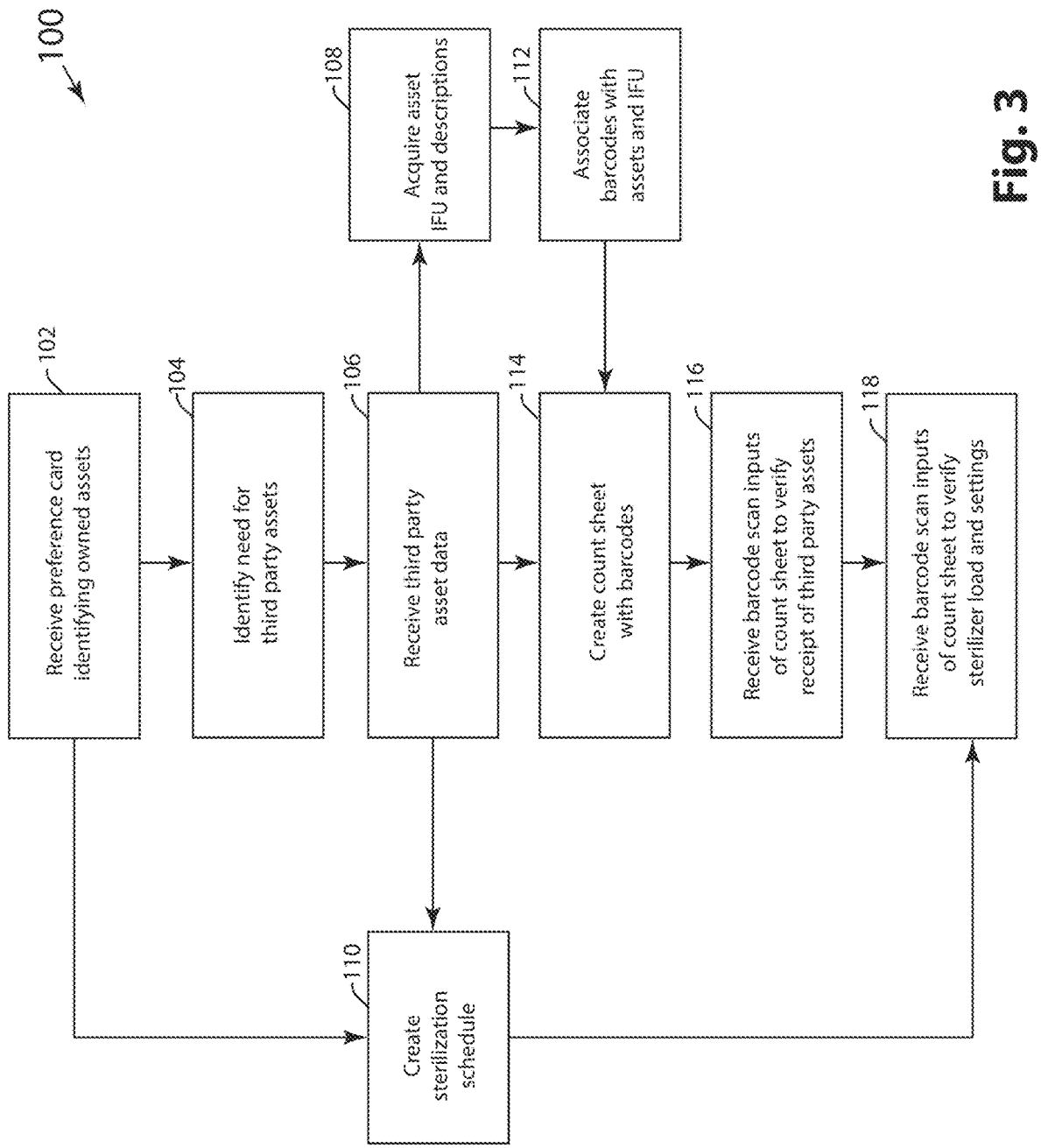
FIG. 3 is a flow chart that depicts an exemplary embodiment of a method of processing third party assets.

FIG. 3 is a flow chart that depicts an exemplary embodiment of a method 100 of processing third party assets. Exemplary embodiments of the method 100 may be carried out by the instrument management systems 10, 60 as described above, and in particular, may be carried out by a sterile processing information system 24 as described above with respect to those systems. In an exemplary embodiment, the sterile processing information system 24 may be implemented with a computer processor that executes computer readable code that upon execution causes the processor to carry out the functions described herein associated with method 100 as well as other embodiments and the other functions as described in the present application.

At 102, a preference card identifying the owned assets required for a surgery is received. A preference card may be produced by a hospital clinical system 20 or a surgery scheduler interface 62, as described in the systems above. The owned assets are those instruments, instrument kits, and consumables owned by the hospital and available for use in the scheduled surgery.

Next, at 104, a need for third party assets is identified. This need for third party assets may be identified by a line item in the preference card indicating one or more loaner sets and/or third party provided implants or other consumables, while in other embodiments a low or unavailable inventory of hospital owned assets, may prompt the system to identify that a third party asset must be borrowed or provided on consignment.

When third party assets are needed, at 106 the third party asset data is received. As described above, the third party asset data may be received from an inventory management system of the third party asset owner and may exemplarily be received at periodic updates, including every 30 seconds, every 90 seconds, or less frequent periodic updates. The received third party asset data may include an identification of all of the instruments, instrument sets, and consumables, including screws, pins, or implants to be provided by the third party.

At 108, the asset instructions for use (IFU) and the descriptions are acquired. In one exemplary embodiment, the asset IFUs and descriptions are received as part of the third party asset data at 106. In an alternative embodiment, the third party asset data is used to acquire the asset IFUs and descriptions from other databases based upon the third party asset data. Once the owned assets are received at 102 and the third party asset data is received at 106, then a sterilization schedule can be created at 110. Since the full bill of material required for the surgery is known by the integration of the identified required owned assets and the third party assets to be received, a complete schedule that incorporates processing requirements of both owned assets and third party assets can be created at 110. By creating a sterilization schedule that incorporates both owned assets and third party assets to be received prior to the surgery, a sterilization schedule that maximizes efficiency in processing and use of staff and sterilization equipment can be constructed.

At 112, barcodes and barcode numbers are associated with each of the third party assets identified in the third party asset data and associated with the IFU for those third party assets.

At 114, a count sheet is created with the barcodes to identify the third party assets. The count sheet is exemplarily printed to physically create the count sheet which is available to personnel when the third party assets are received. Upon receipt of the third party assets, to the hospital, barcode scan inputs are received at 116 of the count sheet barcode to verify receipt of the third party assets by the hospital. When the third party assets are scheduled to be sterilized according to the sterilization schedule created at 110, then barcode scan inputs of the count sheet are received again at 118 to verify the sterilizer load according to the sterilization schedule, as well as the settings of the sterilizer device in accordance with the IFUs of the third party assets associated with the scanned barcode. In addition to the verification processes, the received barcode scanned inputs are stored as documentation that third party assets are received by the hospital and undergo the required sterilization processes.

Figure 4:
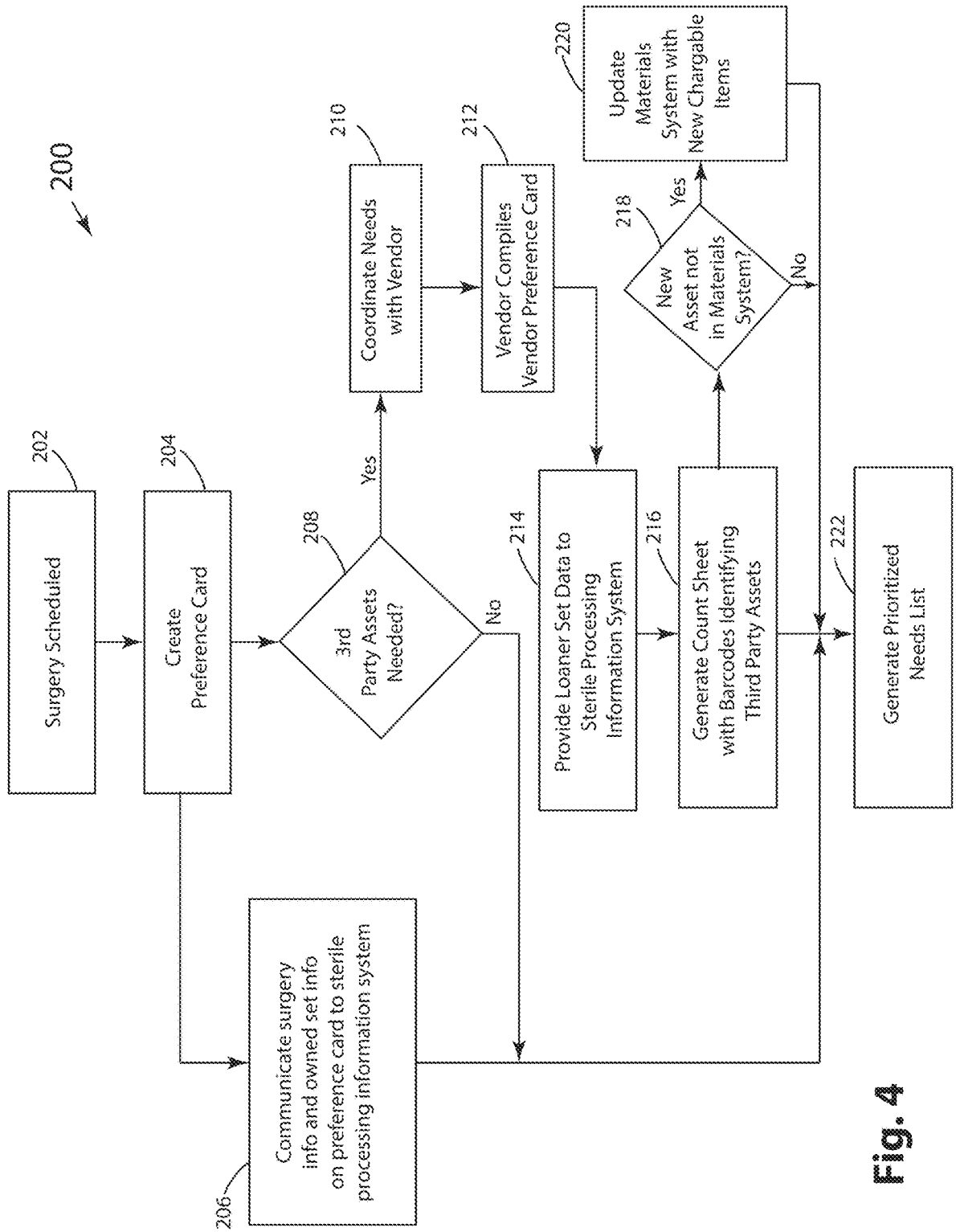
FIG. 4 is a flow chart that depicts an exemplary embodiment of a method of sterile processing department scheduling.

FIG. 4 is a flow chart that depicts an exemplary embodiment of a method to process workflow for sterilization scheduling. It will be recognized that exemplary embodiments of a method 200 may be carried out by the sterile processing information system 24 as described above, in particular with respect to FIG. 1. At 202 a surgery is scheduled. The scheduled surgery may exemplarily be scheduled in the hospital clinical system and identify the relevant surgeon or other personnel, surgical room, times, dates, and other information required to schedule the surgery. At 204 a preference card is created. The preference card includes the information for the scheduled surgery, and also includes an identification of any hospital owned assets, including instruments and consumables required in loaned sets to be used for the surgery. At 206 the hospital surgical system communicates with the sterile processing information system to communicate the information of the preference card from the surgical system to the sterile processing information system. This communicated information provides surgery information for the scheduled surgery as well as the identification of the owned sets to the sterile processing information system. At 208 a determination is made whether or not third party assets are required. If no third party assets are required for the surgery, then the sterile processing information system may operate in a known manner to assist in management of the reprocessing cycle of the owned asset in the sterile processing department. If third party assets are required, than at 210 the system coordinates with the third party owner, e.g., a vendor, to identify the contents of any vendor owned loaner sets to be used in the scheduled surgery. At 212, the vendor compiles and maintains a vendor preference card for the scheduled surgery. The vendor preference card identifies all of the vendor owned assets to be delivered to the hospital for use in the scheduled surgery. The vendor preference card includes loaner set data including identifications of each instrument and/or consumable, instructions for use (IFU), loaner set contents, and referential pictures.

At 214 the loaner set data is provided to the sterile processing information system. In exemplary embodiments the vendor provides the loaner set data to the sterile processing information system, for example by pushing the loaner data to the sterile processing information system every time a vendor preference card is updated with information. In another embodiment, the loaner set data is pushed to the sterile processing information system or retrieved by the sterile processing information system from the vendor at a regular interval or schedule. The loaner set data includes, but is not limited to identifications of loaned assets, contents of loaner sets, instructions for use, pictures the loaner set data may further include surgical case information including a case identifier, a surgeon, and/or a surgery location.

At 216 at least one count sheet is generated with barcode identified third party assets received in the loaner sets. The count sheets are generated by the sterile processing information system in advance of receipt of the lender loaner set into the hospital's sterile processing department. The barcode identify each of the third party asset including instruments and/or consumables to be received by the vendor.

At 218 a determination is made whether any of the assets of the third party asset is a new asset that is not currently documented in the hospital's material system. As explained above, the hospital's material system includes a database of instruments and consumables which may be used by the hospital in the performance of surgeries. The material system identifies instruments and consumables and is maintained to provide accurate billing information associated therewith. If one or more of the third party assets are not in the material system, then the sterile processing information system coordinates with the material system at 220 to update the material system with new chargeable items as provided by the third party asset of the loaner set. After these processes are complete, the system generates a prioritized needs list for the handling of all owned assets and loaner assets in the reprocessing cycle by the sterile processing department. In embodiments of the systems and methods as disclosed herein, this prioritized needs list can be generated prior to delivery of the physical loaner sets to the sterile processing department so that the schedule, staffing, and required resources of the sterile processing department can be planned and accommodated prior to delivery of the loaned assets.

Figure 5:
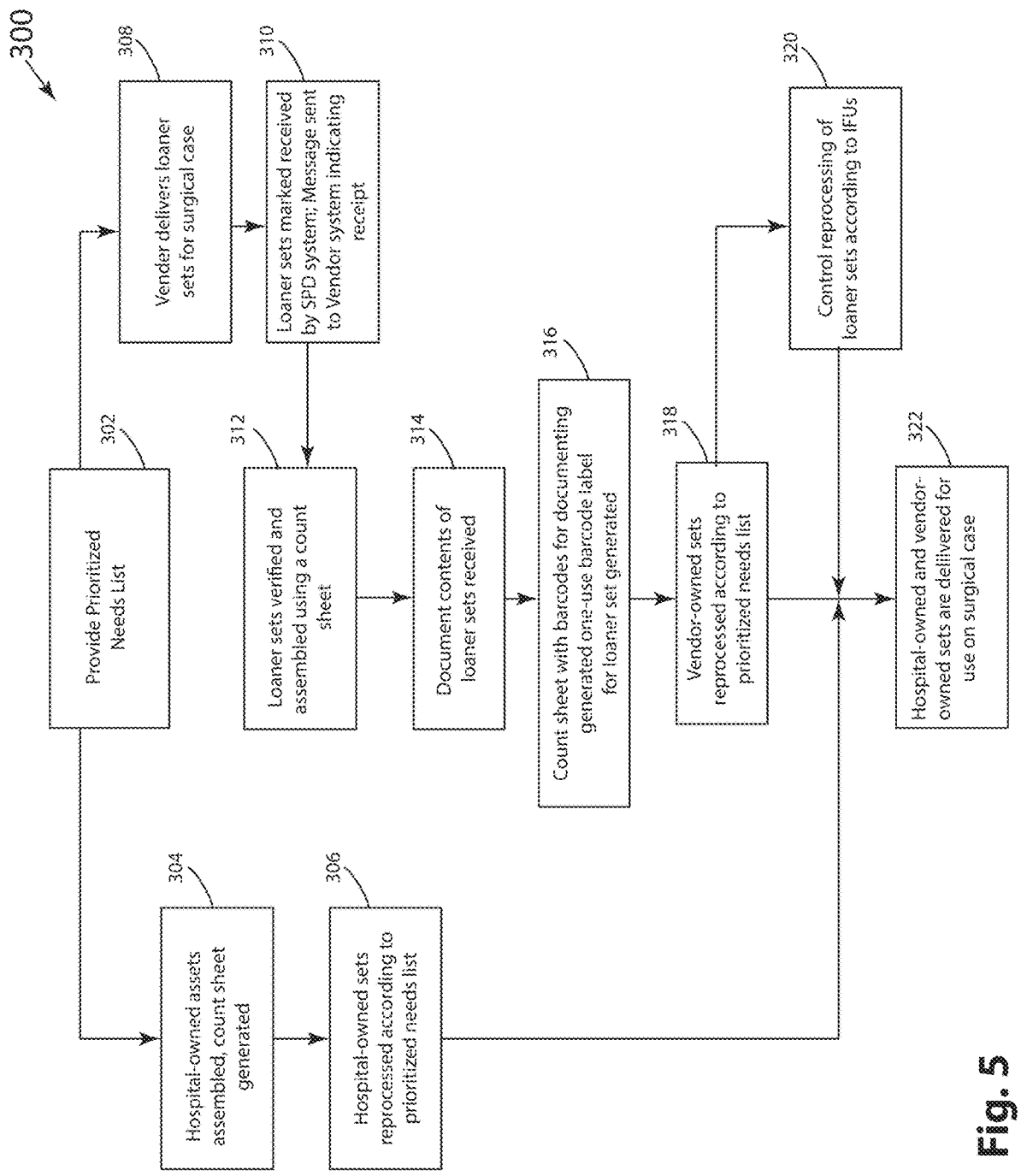
FIG. 5 is a flow chart that depicts an exemplary embodiment of a method of preparing instruments and consumables for surgery.

FIG. 5 is a flow chart that depicts an exemplary embodiment of a method 300 of preparing instruments and consumables for surgery. In an exemplary embodiment, the method 300 picks up from the end of the method 200 described above with respect to FIG. 4. At 302 the prioritized needs list is provided. The prioritized needs list is exemplarily generated as described above at 222 of FIG. 4 and includes all of the required reprocessing tasks for both hospital owned and vendor owned sets of instrumentation and/or consumables. At 304 the hospital owned assets are assembled and a count sheet is generated for the hospital owned assets. The assembled hospital owned assets are reprocessed according to the prioritized needs list at 306. As described above, the reprocessing cycle may include, but is not limited to cleaning, inspection, packaging, and sterilizing. The vendor owned sets are processed in a different manner in accordance with the method 300. At 308 the vendor delivers the loaner sets for the surgery to the sterile processing department. At 310 the loaner sets are marked received by the sterile processing department and a message is sent to the vendor indicating receipt of the loaner sets. At 312, the received loaner sets are verified and assembled using a previously generated count sheet. As a part of the verification and assembly at 312, the contents of the received loaner set is documented at 314. In an exemplary embodiment, this documentation may include identifying instruments or consumables identified on the count sheet but not received in the loaner set and/or taking a digital photograph of the loaner sets in the condition as received.

At 316 if not previously performed, a count sheet with barcodes identifying each item in the loaner sets in generated and a one use barcode label for each loaner set is generated. After which, the loaner sets are reprocessed according to the prioritized needs list by the sterile processing department personnel. As described above, the reprocessing cycle includes cleaning, inspection, packaging, sterilizing. During packaging, the count sheet with barcodes may be placed inside the loaner set packaging and the one use barcode label affixed to the outside of the packaging. Thus, the one use barcode label is used to identify the packaged loaner set between the time when the instruments and consumables are packaged for sterilization, sterilized, and delivered to the surgery site and prior to use of the sterilized instruments and consumables of the loaner set during surgery.

At 320 individual steps in the reprocessing cycle are performed according to the instructions for use (IFU) for the particular loaner sets. In exemplary embodiments depending upon the process of the reprocessing cycle, the barcode of the count sheet and/or the one-use barcode for the loaner set embodied and identification or pointer to verify or identify IFU particular to the instrument and/or loaner set. Thus, through the use of the count sheet with barcodes and/or the one-used barcode label for the loaner sets, IFU documentation can be readily accessed by thorough processing department personnel through the reprocessing cycle.

After reprocessing, at 322 the hospital owned assets and the vendor owned loaner sets are delivered to the surgery location for use in the surgical case.

Figure 6:
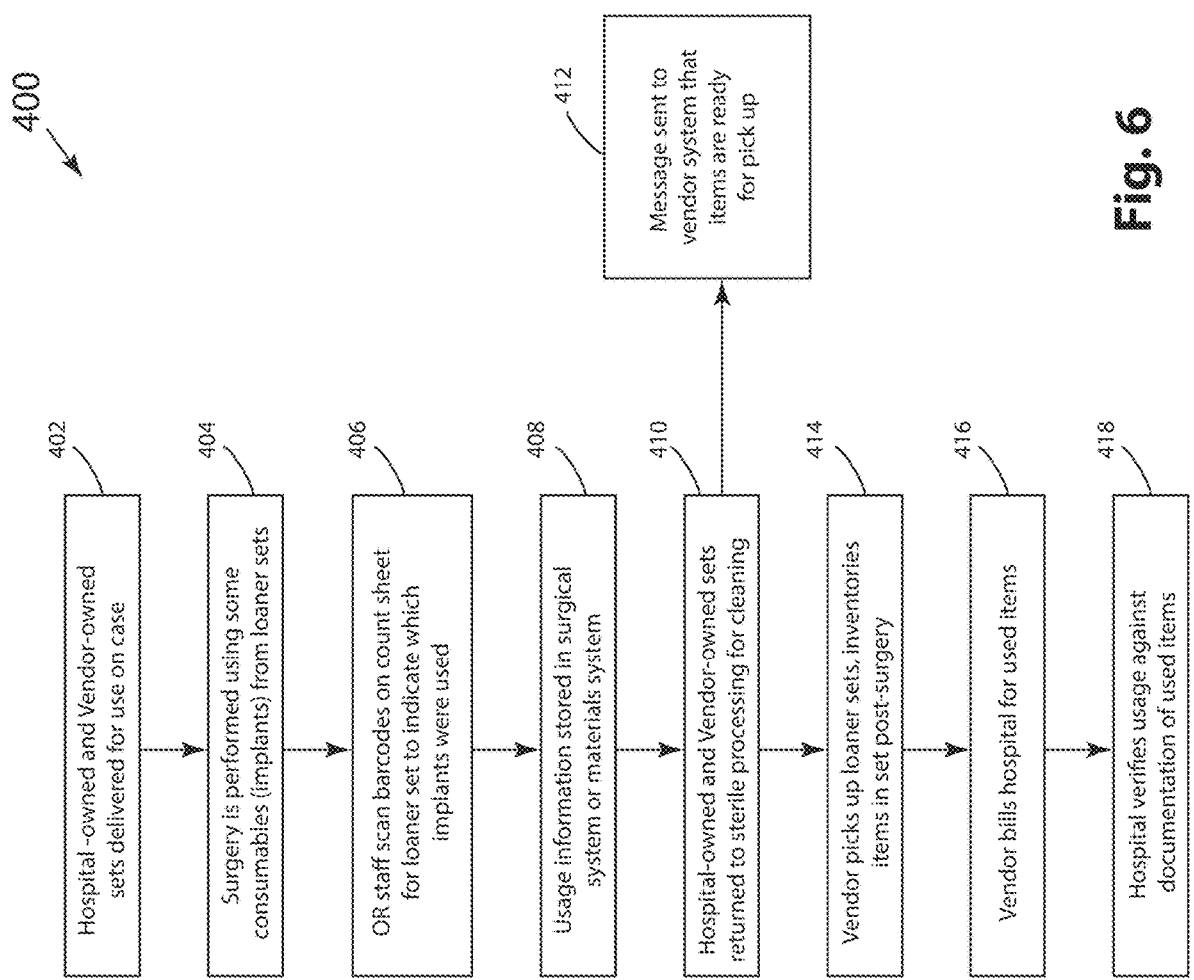
FIG. 6 is a flow chart that depicts an exemplary embodiment of a method of documenting of a method of documenting instrument and consumable use during surgery.

FIG. 6 is a flow chart that depicts an exemplary embodiment of a method 400 of documenting instrument and consumable use during surgery. In an exemplary embodiment, the method 400 may be performed subsequent to the method 300 described above, beginning with the hospital owned and vendor owned sets being processed as described above with respect to the method 300 and delivered to a surgical site for use in a surgical case. At 404 the surgery is performed using at least one consumable (e.g. implant) from a loaner set. At 406 the operating room staff retrieves the associated count sheet from the loaner set from which the consumable is used and scans the associated barcode on the count sheet to indicate to the hospital surgical system which consumables were used.

The identification, usage, and/or charging information embodied in the barcode on the count sheet is stored in the hospital surgical system or in the material system at 408. In another embodiment, search information is first stored at the hospital surgical system and later transferred to the material system for charging and verification.

At 410 hospital owned and vendor owned sets including instrumentation and unused consumables are returned to the sterile processing department for cleaning. In embodiments, at 412 a message is sent to the vendor to schedule pickup of the loaner sets. At 414 the vendor picks up the clean loaner sets from the sterile processing department and inventories the items in the returned loaner set post surgery. In embodiments, and particularly in consignment embodiments, the vendor bills the hospital at 416 for the consumables used, and therefore not in the returned loaner set. As an additional advantage of embodiments of the method 400, the hospital uses the documentation information obtained from scanning the barcodes during the surgery at 406 to verify the vendor's bill at 418 against the hospital's documentation of used items.

FIG. 7 depicts an exemplary embodiment of a count sheet 700 as generated and used within the systems and methods as disclosed herein. The count sheet 700 exemplarily includes a list of the identified instruments 702 and/or consumables in a particular loaner set and a barcode 704, exemplarily a 2D barcode, associated with each of these line items on the count sheet. In an exemplary embodiment, the barcode 704 is a quick response (QR) code.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of management of surgical assets, the method comprising:
   receiving, at a sterile processing information system from a hospital clinical system, a hospital preference card identifying a scheduled surgery and a plurality of required owned assets for the scheduled surgery;

associating data for the plurality of required owned assets with the scheduled surgery in the sterile processing information system;

receiving a vendor preference card for the scheduled surgery at a vendor inventory management system;

upon receiving the vendor preference card, automatically creating parsable third party asset data in structured format for third party assets identified in the vendor preference card;

electronically transmitting, by an application program interface associated with the vendor inventory management system, the parsable third party asset data in structured format for the third party assets identified in the vendor preference card to an interface service for the sterile processing information system, wherein the parsable third party asset data in structured format includes at least a case identifier for the scheduled surgery and a loaner set identifier;

receiving, at the interface service of the sterile processing information system, said electronically transmitted third party asset data prior to receipt of the identified third party assets;

determining whether the third party asset data is associated with a known asset record in the sterile processing information system based on the loaner set identifier included with the third party asset data;

automatically acquiring, by the interface service of the sterile processing information system prior to receipt of the identified third party assets, instructions for use (IFU) and descriptions for each of the identified third party assets responsive to a determination that the third party asset data is not associated with a known asset record;

integrating the third party asset data into the sterile processing information system and associating the third party asset data with the scheduled surgery using the case identifier for the scheduled surgery in the third party asset data such that the data for the plurality of owned assets and the third party set data for the scheduled surgery are integrated within the sterile processing system;

creating, at the sterile processing information system, a sterilization schedule based upon the plurality of required owned assets, identified third party assets, and the instructions for use of the identified third party assets;

creating, at the sterile processing information system, a count sheet with a plurality of barcodes associated with the identified third party assets;

verifying, at the sterile processing information system, receipt of the identified third party assets by the hospital by receiving a barcode scan input of a barcode from the count sheet; and verifying, at the sterile processing information system, a load in a sterilizer and sterilizer settings according to the sterilization schedule by receiving a barcode scan input of a barcode from the count sheet.

2. The method of claim 1, wherein the identified third party assets are received in a plurality of asset trays and creating a count sheet further comprises creating a count sheet for each of the plurality of asset trays.

3. The method of claim 1, wherein the identified third party assets comprises at least one surgical implant.

4. The method of claim 1, wherein the steps of receiving barcode scan inputs further comprise documenting the barcode scan inputs with a time and a date to track receipt and processing of the third party assets within the hospital.

5. The method of claim 1, wherein the third party asset data is received from an inventory management system of a third party.

6. The method of claim 5, wherein the third party asset data is received from the inventory management system at periodic intervals.

7. The method of claim 1, further comprising verifying, from the received barcode scan input, the sterilizer settings in accordance with the IFU of identified third party assets associated with the received barcode scan inputs.

8. The method of claim 1, further comprising:
packaging the sterilized third party assets with sterilized owned assets for use in surgery;
providing the packaged sterilized third party assets with the count sheet for the third party assets;
creating a count sheet for the sterilized owned assets; and
providing the sterilized owned assets with the count sheet for the sterilized owned assets.

9. The method of claim 8, further comprising:
receiving a plurality of bar code scan inputs of the count sheets;
documenting use of each of the identified third party assets and owned assets associated with the plurality of bar code scan inputs.

10. The method of claim 1, further comprising:
verifying return of each of the identified third party asset after completion of a surgical procedure by receiving a barcode scan input of a barcode from the count sheet.

* * * * *